United States Patent [19]

Bird et al.

[11] Patent Number: 5,352,793

[45] Date of Patent: Oct. 4, 1994

[54] SUNSCREEN COMPOUNDS

[75] Inventors: Graham Bird; Neil Fitzmaurice, both of Victoria; Walter C. Dunlap, Queensland; Bruce E. Chalker, Queensland; Wickramasinghe M. Bandaranayake, Queensland, all of Australia

[73] Assignee: ICI Australia Operations Proprietary Limited, Melbourne, Australia

[21] Appl. No.: 618,610

[22] Filed: Nov. 27, 1990

Related U.S. Application Data

[62] Division of Ser. No. 236,530, May 26, 1988, Pat. No. 5,100,496.

[30] Foreign Application Priority Data

Sep. 26, 1986 [AU] Australia .................. PH8208
Nov. 25, 1986 [AU] Australia .................. PH9230

[51] Int. Cl.$^5$ ................. C07D 213/30; C07D 213/46
[52] U.S. Cl. ........................... 546/315; 546/298
[58] Field of Search ............ 546/340, 290, 296, 298, 546/315

[56] References Cited

U.S. PATENT DOCUMENTS 3,479,327 11/1969 Merijan .................. 424/59
3,873,537 3/1975 Parker et al. ............ 424/59

OTHER PUBLICATIONS

CA64:19548c (1966).
Dorofeenko et al., Khim. Geter. Soedin., Akad. Nauk. Latv. SSR (1965) 6, 817–21.

Primary Examiner—Marianne M. Cintins
Assistant Examiner—Phyllis G. Spivack
Attorney, Agent, or Firm—Cushman, Darby & Cushman

[57] ABSTRACT

The invention relates to sunscreen compounds of formula I

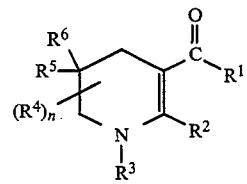

wherein $R^1$ is selected from alkyl, alkenyl, alkynyl substituted alkyl, substituted alkenyl, phenyl, substituted phenyl, substituted benzyl, cycloalkyl, cycloalkenyl, substituted cycloalkyl, substituted cycloalkenyl;

$R^2$ is selected from hydrogen, alkyl and alkoxy;

$R^3$ is selected from alkyl, substituted alkyl, alkenyl, substituted alkenyl, alkynyl, phenyl, benzoyl, substituted phenyl, substituted benzyl, substituted benzoyl, cycloalkyl, substituted cycloalkyl, cycloalkenyl, substituted cycloalkenyl, alkanyoyl, substituted alkanoyl, the group OROROR$^9$ wherein R is a bivalent hydrocarbon radical and $R^9$ is alkyl, alkenyl, phenyl benzyl, substituted phenyl, substituted benzyl;

$R^4$ is alkyl or alkoxy;

n is an integer from 0 to 4; and $R^5$ and $R^6$ are independently selected from alkyl, alkoxy, alkanoyl, alkanoyl substituted by hydroxyl or alkoxycarbonyl.

11 Claims, No Drawings

SUNSCREEN COMPOUNDS

This is a division of application Ser. No. 07/236,530, filed May 26, 1988, now U.S. Pat. No. 5,100,496.

The invention relates to sunscreen compositions comprising ultra-violet radiation absorbing compounds to methods of preparing such compositions, and to UV-absorbing compounds of particular use in preparing such compositions.

Sunscreen compositions may be used to form a coating for protecting substrates from harmful effects of ultraviolet radiation such as in solar radiation. For example, sunscreen compositions are probably best known for use in the protection of skin against severe erythra edema which can be caused by exposure to sunlight.

Common commercially available UV-agents include, for example, para-aminobenzoic acid derivatives, benzotriazoles, benzophenones, methoxycinnamates and salicylates. It has been proposed, for example in U.K. Patent Application 2,120,549A and French Patent Application 8301391, that certain specific classes of vinylagous amide compounds (enaminoketones) may also be used as UV-absorbing sunscreen agents.

We have observed that certain mycosporine amino acids which exist in the living tissue of the Pacific staghorn coral *Acropora formosa* are functional UV-absorbing agents ($\lambda$max 310–332 nm) in corals inhabiting the shallow-water, tropical coral reef environment. While these naturally occurring enaminoketone compounds appear to be potentially attractive as commercial UV-agents, their utility is questionable because of the difficulty of isolating them from their biological source and because of their lack of adequate chemical stability. We have proposed that certain synthetic vinylagous amide analogues of those natural products can be prepared which preserves their characteristic UV-absorbing chromophore within a chemically more stable structure and which typically have UV-absorption maxima ($\lambda$max) in the wavelength region 288–340 nanometers (P.C.T. Patent Application PCT/AU85/00242). These synthetic analogues, however, proved to be chemically unstable during prolonged period of formulation and storage.

We have now found that a select group of cyclic vinylogous amide compounds which comprise a tetrahydropyridine moiety are particularly suitable for use in sunscreen compositions.

Accordingly we provide a sunscreen composition comprising as an effective component thereof at least one compound of formula I

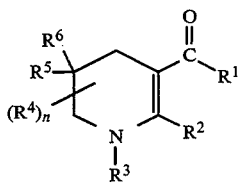

wherein:

$R^1$ is selected from the group consisting of: $C_1$ to $C_{18}$ alkyl; $C_1$ to $C_9$ alkyl substituted with a substituent selected from the group of hydroxy, amino, $C_1$ to $C_9$ alkoxy, $C_2$ to $C_9$ alkenyloxy, $C_1$ to $C_9$ alkanoyl, ($C_1$ to $C_9$ alkoxy)carbonyl, carbamoyl, ($C_1$ to $C_6$ alkyl)carbamoyl and phenyl; $C_2$ to $C_{18}$ alkenyl; $C_2$ to $C_9$ alkenyl substituted with a substituent selected from the group consisting of hydroxy, amino, $C_1$ to $C_9$ alkoxy, $C_2$ to $C_9$ alkenyloxy, $C_1$ to $C_9$ alkanoyl, carbamoyl, ($C_1$ to $C_6$ alkyl)carbamoyl, and phenyl; $C_2$ to $C_{18}$ alkynyl; phenyl; the groups phenyl and benzyl said groups being substituted in the benzene ring with a substituent is selected from the group of $C_1$ to $C_{12}$ alkyl, $C_1$ to $C_{12}$ alkoxy, $C_1$ to $C_{12}$ alkenyloxy, $C_1$ to $C_{12}$ alkylamino, N,N-di($C_1$ to $C_6$ alkyl)amino, ($C_1$ to $C_{12}$ alkoxy)carbonyl and $C_1$ to $C_{12}$ alkanoyl; $C_5$ to $C_7$ cycloalkyl; $C_5$ to $C_7$ cycloalkenyl; the groups substituted $C_5$ to $C_7$ cycloalkyl and substituted $C_5$ to $C_7$ cycloalkenyl wherein the substituent is selected from the group of hydroxy, amino, $C_1$ to $C_9$ alkyl, $C_1$ to $C_9$ alkoxy, and $C_1$ to $C_9$ alkenyloxy; polymers of one or more of the monomers selected from ethylene glycol, propylene glycol, styrene and $C_2$ to $C_4$ alkenes, and derivatives of said polymers; and wherein $R^1$ may optionally link together with $R^2$ via a bridging group of formula —$(R^7R^8C)_m$- wherein m is 2 or 3 and $R^7$ (which may be the same or different) and $R^8$ (which may be the same or different) are independently selected from the group of hydrogen and $C_1$ to $C_6$ alkyl;

$R^2$ is selected from the group consisting of hydrogen, $C_1$ to $C_6$ alkyl, $C_1$ to $C_6$ alkoxy, and the group wherein $R^1$ and $R^2$ together form a bridging group of formula —$(CH^7R^8)_m$— wherein $R^7$, $R^8$ and m are as hereinbefore defined;

$R^3$ is selected from the group consisting of: $C_1$ to $C_{18}$ alkyl; $C_1$ to $C_9$ alkyl substituted with a substituent selected from the group of amino, $C_1$ to $C_9$ alkoxy, $C_2$ to $C_9$ alkenyloxy, $C_1$ to $C_9$ alkanoyl, ($C_1$ to $C_9$ alkoxy)carbonyl, carbamoyl, ($C_1$ to $C_6$ alkyl)carbamoyl, and phenyl; $C_2$ to $C_{18}$ alkenyl; $C_2$ to $C_9$ alkenyl substituted with a substituent selected from the group consisting of hydroxy, amino $C_1$ to $C_9$ alkoxy, $C_2$ to $C_9$ alkenyloxy, $C_1$ to $C_9$ alkanoyl, ($C_1$ to $C_9$ alkoxy)carbonyl, carbamoyl, ($C_1$ to $C_9$ alkyl)carbamoyl and phenyl; $C_2$ to $C_{18}$ alkynyl; phenyl; benzoyl; the groups phenyl, benzyl and benzoyl said group being substituted in the benzene ring with a substituent selected from the group of hydroxy, amino, $C_1$ to $C_{12}$ alkyl, $C_2$ to $C_{12}$ alkenyl, $C_1$ to $C_{12}$ alkoxy, $C_2$ to $C_{12}$ alkenyloxy, $C_1$ to $C_{12}$ alkylamino, N,N-di($C_1$ to $C_6$ alkyl)amino, ($C_1$ to $C_{12}$ alkoxy)carbonyl, and $C_1$ to $C_{12}$ alkanoyl; $C_5$ to $C_7$ cycloalkyl; $C_5$ to $C_7$ cycloalkenyl; the groups substituted $C_5$ to $C_7$ cycloalkyl and substituted $C_5$ to $C_7$ cycloalkenyl wherein the substituent is selected from the group of hydroxy, amino, $C_1$ to $C_9$ alkyl, $C_1$ to $C_9$ alkoxy, and $C_1$ to $C_9$ alkenyloxy; $C_1$ to $C_{18}$ alkanoyl; $C_2$ to $C_9$ alkanoyl substituted with a substituent selected from the group of hydroxy, amino, $C_1$ to $C_9$ alkoxy and $C_2$ to $C_9$ alkenyloxy, $C_1$ to $C_9$ alkanoyl; carbamoyl, ($C_1$ to $C_6$ alkyl)carbamoyl, ($C_1$ to $C_9$ alkoxy)carbonyl and phenyl; polymers of one or more monomers selected from ethylene glycol, propylene glycol, styrene and $C_2$ to $C_4$ alkenes, and derivatives of said polymers; and the group —OROROR$^9$ wherein R (which may be the same or different) is a bivalent hydrocarbon radical of 2 to 6 (more preferably 2 to 4) carbon atoms and $R^9$ is a hydrocarbon radical selected from $C_1$ to $C_6$ alkyl, $C_2$ to $C_6$ alkenyl, phenyl, benzyl, $C_1$ to $C_6$ alkyl phenyl and ($C_1$ to $C_6$ alkyl)benzyl (more preferably $R^9$ is selected from $C_1$ to $C_4$ alkyl and $C_2$);

$R^4$ is selected from the group consisting of $C_1$ to $C_6$ alkyl and $C_1$ to $C_6$ alkoxy;

n is an integer selected from 0 to 4 inclusive; and $R^5$ and $R^6$ which maybe the same or different are selected from hydrogen, $C_1$ to $C_6$ alkyl, $C_1$ to $C_6$ alkoxy, $C_1$ to $C_{10}$ alkanoyl, $C_1$ to $C_{10}$ alkanoyl substituted by carboxyl or ($C_1$ to $C_6$ alkoxy)carbonyl and wherein $R^5$ and $R^6$ may form a spiro-carbocyclic ring by the bridging group of formula II $$-\overset{O}{\underset{\|}{C}}-(CR^{10}R^{11})_q-\overset{O}{\underset{\|}{C}}- \quad \text{II}$$

wherein q is 2 or 3 and $R^{10}$ and $R^{11}$ may be the same or different at each carbon unit of the bridge and are independently selected from hydrogen and $C_1$ to $C_8$ alkyl.

The composition of the present invention may be applied to a surface to reduce the exposure of the surface to ultra-violet radiation. The composition may be formulated, for example, as a solid, liquid, gel or aerosol and may generally comprise a carrier (extending medium) which adapts the agent for application to a surface.

In a further embodiment of the invention, there is provided a method of preparation of a sunscreen composition comprising mixing at least one compound of formula I with a carrier suitably adapted to allow application of said compound to a surface. Examples of suitable carriers may include oils for example, mineral oils, paraffin, squalene and octyl palmetate and oil/alcohol mixtures.

In a specific example, at least one compound of formula I is combined with a water-insoluble liquid such as a paraffin oil to give an oil phase which is combined with an aqueous phase to form an oil-in-water emulsion in the presence of a suitable emulsifier.

The temperature at which the composition is formed is not critical and may be selected in accordance with the nature of to the components thereof. The temperature is typically in the range 0° to 150° C. (preferably 0° to 80°) although higher or lower temperatures may be used if desired.

Further components such as perfumes, colouring agents, antioxidants and oxygen scavengers may be used in the composition of the present invention.

Examples of oxygen scavengers include compounds which in the presence of oxygen are oxidised more readily than the compound of formula I. An example of an oxygen scavenger is sodium thiosulphate.

The composition may comprise additives making the composition useful as a cosmetic or phamaceutical.

One or more compounds of formula I may be utilized in the composition of the present invention and generally the concentration of said compound(s) is in the range of 0.5 to 20% by weight of the total composition. However higher or lower concentrations may be used if desired depending on the degree of screening required.

Preferably in the compound of formula I $R^1$ is selected from $C_1$ to $C_{18}$ alkyl;

$C_1$ to $C_9$ alkyl substituted with a substitutent selected from the group consisting of, hydroxy, amino, $C_1$ to $C_9$ alkoxy; $C_1$ to $C_9$ alkanoyl and ($C_1$ to $C_9$ alkoxy)carbonyl; $C_1$ to $C_{18}$ alkenyl; cyclohexyl; phenyl; benzyl; the groups phenyl and benzyl said groups being substituted in the benzene ring with a substituent selected form the group of $C_1$ to $C_9$ alkyl, $C_2$ to $C_9$ alkenyl, $C_1$ to $C_9$ alkoxy, $C_1$ to $C_9$ alkylamino, N,N-di($C_1$ to $C_6$ alkyl)amino, $C_1$ to $C_9$ alkanoyl and ($C_1$ to $C_9$ alkoxy)carbonyl; and wherein $R^1$ may optionally link together with $R^2$ via a bridging group of formula $-CH_2(R^7R^8C)CH_2-$ wherein $R^7$ and $R^8$ are independently selected from hydrogen and $C_1$ to $C_6$ alkyl;

$R^3$ is selected from $C_1$ to $C_{18}$ alkyl; $C_1$ to $C_9$ alkyl substituted with a substituent selected form the group consisting of hydroxy, amino, $C_1$ to $C_9$ alkoxy and $C_1$ to $C_9$ alkanoyl; $C_2$ to $C_{18}$ alkenyl; cyclohexyl; phenyl; benzyl; benzoyl; the groups phenyl, benzyl and benzoyl said groups being substituted in the benzene ring with a substituent selected from the group of $C_1$ to $C_9$ alkyl, $C_2$ to $C_9$ alkenyl, $C_1$ to $C_9$ alkoxy, $C_1$ to $C_9$ alkylamino, N,N-di($C_1$ to $C_6$ alkyl)amino, $C_1$ to $C_9$ alkanoyl and ($C_1$ to $C_9$ alkoxy)carbonyl; $C_1$ to $C_{18}$ alkanoyl; and $C_2$ to $C_9$ alkanoyl substituted with phenyl;

$R^2$ is selected from hydrogen and $C_1$ to $C_6$ alkyl; and wherein $R^2$ may link together with $R^1$ to form a bridging group of formula $-CH_2(R^7R^8C)CH_2-$ wherein $R^7$ and $R^8$ are independently selected from hydrogen and $C_1$ to $C_6$ alkyl;

$R^4$ is $C_1$ to $C_6$ alkyl; and n is from 0 to 4, and $R^5$ and $R^6$ are independently selected from hydrogen; the group of formula III $$-\overset{O}{\overset{\|}{C}}(CH_2)(CR^{10}R^{11})CH_2\overset{O}{\overset{\|}{C}}OR^{12} \qquad \text{III}$$

$R^{10}$ and $R^{11}$ are independently selected from $C_1$ to $C_4$ alkyl and hydrogen; and $R^{12}$ is selected from hydrogen and $C_1$ to $C_6$ alkyl and wherein $R^5$ and $R^6$ may form a spiro-carbocyclic ring by the bridging group of formula II (a)

$$-\overset{O}{\overset{\|}{C}}CH_2-(CR^{10}R^{11})-CH_2\overset{O}{\overset{\|}{C}}- \qquad \text{II(a)}$$

wherein $R^{10}$ and $R^{11}$ are independently selected from hydrogen and $C_1$ to $C_4$ alkyl.

Preferably wherein one of $R^5$ and $R^6$ is the group of formula III then the other is hydrogen.

More preferred $R^1$ compositions of the invention comprise at least one compound of formula I wherein:

$R^1$ is selected from the group consisting of $C_1$ to $C_{18}$ alkyl; $C_1$ to $C_{18}$ alkenyl; phenyl; and benzyl;

$R^2$ is hydrogen or $C_1$ to $C_4$ alkyl; and wherein $R^1$ and $R^2$ may form a carbocyclic ring by the bridging group of formula $$-CH_2(CR^7R^8)CH_2-$$

wherein $R^7$ and $R^8$ are independently selected from hydrogen and $C_1$ to $C_4$ alkyl;

$R^3$ is selected from $C_2$ to $C_{18}$ alkyl; $C_1$ to $C_9$ alkyl substituted with a substituent selected from the group consisting of hydroxy and $C_1$ to $C_9$ alkoxy; $C_1$ to $C_{18}$ alkenyl; benzoyl; benzyl; benzoyl substituted with a substituent selected from $C_1$ to $C_6$ alkyl and $C_1$ to $C_6$ alkoxy; and $C_1$ to $C_9$ alkanoyl;

$R^4$ is $C_1$ to $C_4$ alkyl n is from 0 to 3

$R^5$ and $R^6$ are selected such that they comply with one of the possibilities selected from the group consisting of (i) $R^5$ and $R^6$ are independently selected from hydrogen and $C_1$ to $C_4$ alkyl; (ii) one of $R^5$ and $R^6$ is hydrogen and the other is a group of formula III

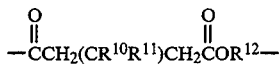

$$-CCH_2(CR^{10}R^{11})CH_2COR^{12}- \quad \text{III}$$

wherein $R^{10}$, $R^{11}$ and $R^{12}$ are independently selected from the group consisting of hydrogen and $C_1$ to $C_4$ alkyl; and (iii) the group wherein $R^5$ and $R^6$ form a spiro carbocyclic ring by the group of formula IIa

$$-CCH_2(CR^{10}R^{11})CH_2C- \quad \text{IIa}$$

wherein $R^{10}$ and $R^{11}$ are independently selected from the group consisting of hydrogen and $C_1$ to $C_4$ alkyl.

In a particularly preferred group of compositions of the invention the compound of formula I is selected such that $R^1$ is selected from the group consisting of $C_1$ to $C_{18}$ alkyl; $C_1$ to $C_{18}$ alkenyl; phenyl; and benzyl;

$R^2$ is hydrogen or $C_1$ to $C_4$ alkyl; and wherein $R^1$ and $R^2$ may form a carbocyclic ring by the bridging group of formula

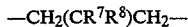

$$-CH_2(CR^7R^8)CH_2-$$

wherein $R^7$ and $R^8$ are independently selected from hydrogen and $C_1$ to $C_4$ alkyl;

$R^3$ is selected from $C_1$ to $C_{18}$ alkyl;

$C_2$ to $C_{18}$ alkenyl; benzoyl; benzyl; benzoyl substituted with a substituent selected from $C_1$ to $C_6$ alkyl and $C_1$ to $C_6$ alkoxy; and $C_3$ to $C_9$ alkanoyl;

$R$ is $C_1$ to $C_4$ alkyl;

n is from 0 to 3; and $R^5$ and $R^6$ are independently selected from hydrogen and $C_1$ to $C_4$ alkyl.

Many of the compounds for use in preparing of compositions of the inventions are novel compounds.

According to a further embodiment of the invention there is therefore provided a compound of formula I

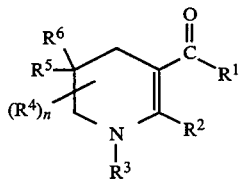

wherein:

$R^1$ is selected from the group consisting of: $C_1$ to $C_{18}$ alkyl; $C_1$ to $C_9$ alkyl substituted with a substituent selected from the group of hydroxy, amino, $C_1$ to $C_9$ alkoxy, $C_2$ to $C_9$ alkenyloxy, $C_1$ to $C_9$ alkanoyl, ($C_1$ to $C_9$ alkoxy)carbonyl, carbamoyl, ($C_1$ to $C_6$ alkyl)carbamoyl and phenyl; $C_2$ to $C_{18}$ alkenyl; $C_2$ to $C_9$ alkenyl substituted with a substituent selected from the group consisting of hydroxy, amino, $C_1$ to $C_9$ alkoxy, $C_2$ to $C_9$ alkenyloxy, $C_1$ to $C_9$ alkanoyl, carbamoyl, ($C_1$ to $C_6$ alkyl)carbamoyl, and phenyl; $C_2$ to $C_{18}$ alkynyl; phenyl; the groups phenyl and benzyl said groups being substituted in the benzene ring with a substituent selected from the group of $C_1$ to $C_{12}$ alkyl, $C_1$ to $C_{12}$ alkoxy, $C_1$ to $C_{12}$ alkenyloxy, $C_1$ to $C_{12}$ alkylamino, N,N-di-($C_1$ to $C_6$ alkyl)amino, ($C_1$ to $C_{12}$ alkoxy)carbonyl and $C_1$ to $C_{12}$ alkanoyl; $C_5$ to $C_7$ cycloalkyl; $C_5$ to $C_7$ cycloalkenyl; the groups substituted $C_5$ to $C_7$ cycloalkyl and substituted $C_5$ to $C_7$ cycloalkenyl wherein the substituent is selected from the group of hydroxy, amino, $C_1$ to $C_9$ alkyl, $C_1$ to $C_9$ alkoxy, and $C_1$ to $C_9$ alkenyloxy; polymers of one or more of the monomers selected from ethylene glycol, propylene glycol, styrene and $C_2$ to $C_4$ alkenes, and derivatives of said polymers; and wherein $R^1$ may optionally link together with $R^2$ to form a carbocyclic ring by the bridging group of formula $-(R^7R^8C-)m-$ wherein m is 2 or 3 and $R^7$ (which may be the same or different) and $R^8$ (which may be the same or different) are independently selected from the group of hydrogen and $C_1$ to $C_6$ alkyl;

$R^3$ is selected from the group consisting of: $C_2$ to $C_{18}$ alkyl; $C_1$ to $C_9$ alkyl substituted with a substituent selected from the group of amino, $C_1$ to $C_9$ alkoxy, $C_2$ to $C_9$ alkenyloxy, $C_1$ to $C_9$ alkanoyl, ($C_1$ to $C_9$ alkoxy)carbonyl, carbamoyl, ($C_1$ to $C_6$ alkyl)carbamoyl and phenyl; $C_2$ to $C_{18}$ alkenyl; $C_2$ to $C_9$ alkenyl substituted with a substituent selected from the group consisting of hydroxy, amino $C_1$ to $C_9$ alkoxy, $C_2$ to $C_9$ alkenyloxy, $C_1$ to $C_9$ alkanoyl, ($C_1$ to $C_9$ alkoxy)carbonyl, carbamoyl, ($C_1$ to $C_9$ alkyl) carbamoyl and phenyl; $C_2$ to $C_{18}$ alkynyl; phenyl; benzoyl; the groups phenyl, benzyl and benzoyl said groups being substituted in the benzene ring with a substituent selected from the group of hydroxy, amino, $C_1$ to $C_{12}$ alkyl, $C_2$ to $C_{12}$ alkenyl, $C_1$ to $C_{12}$ alkoxy, $C_2$ to $C_{12}$ alkenyloxy, $C_1$ to $C_{12}$ alkylamino, N,N-di-($C_1$ to $C_6$ alkyl)amino, ($C_1$ to $C_{12}$ alkoxy)carbonyl, and $C_1$ to $C_{12}$ alkanoyl; $C_5$ to $C_7$ cycloalkyl; $C_5$ to $C_7$ cycloalkenyl; the groups substituted $C_5$ to $C_7$ cycloalkyl and substituted $C_5$ to $C_7$ cycloalkenyl wherein the substituent is selected from the group of hydroxy, amino, $C_1$ to $C_9$ alkyl, $C_1$ to $C_9$ alkoxy, and $C_1$ to $C_9$ alkenyloxy; $C_1$ to $C_{18}$ alkanoyl; $C_1$ to $C_9$ alkanoyl substituted with a substituent selected from the group of hydroxy, amino, $C_1$ to $C_9$ alkoxy and $C_2$ to $C_9$ alkenyloxy, $C_1$ to $C_9$ alkanoyl; carbomoyl, $C_1$ to $C_6$ alkyl)carbamoyl, ($C_1$ to $C_9$ alkoxy)carbonyl and phenyl; polymers of one or more monomers selected from ethylene glycol, propylene glycol, styrene and $C_2$ to $C_4$ alkenes, and derivatives of said polymers; and the group $-OROROR^9$ wherein $R$ (which may be the same or different) is a bivalent hydrocarbon radical of 2 to 6 (more preferably 2 to 4) carbon atoms and $R^9$ is a hydrocarbon radical selected from $C_1$ to $C_6$ alkyl, $C_2$ to $C_6$ alkenyl, phenyl, benzyl, ($C_1$ to $C_6$ alkyl) phenyl and ($C_1$ to $C_6$ alkyl)benzyl (more preferably $R^9$ is selected from $C_1$ to $C_4$ alkyl and $C_2$ to $C_4$ alkenyl);

$R^2$ is selected from the group consisting of hydrogen, $C_1$ to $C_6$ alkyl, and the group wherein $R^1$ and $R^2$ together form a bridging group of formula $-(CR^7R^8)_m-$ wherein $R^7$, $R^8$ and m are as hereinbefore defined;

$R^4$ is selected from the group consisting of $C_1$ to $C_6$ alkyl and $C_1$ to $C_6$ alkoxy;

n is an integer selected from 0 to 4 inclusive; and $R^5$ and $R^6$ which may be the same or different are selected from hydrogen, $C_1$ to $C_6$ alkyl, $C_1$ to $C_6$ alkoxy $C_1$ to $C_{10}$ alkanoyl, $C_1$ to $C_{10}$ alkanoyl substituted by carboxyl or ($C_1$ to $C_6$ alkoxy)carbonyl and wherein $R^7$ and $R^8$ may form a spiro-carbocylic ring by the bridging group of formula II

$$-C-(CR^{10}R^{11})_q-C- \quad \text{II}$$

wherein q is 2 or 3 and $R^{10}$ and $R^{11}$ may be the same or different at each carbon unit of the bridge and are independently selected from hydrogen and $C_1$ to $C_8$ alkyl; with the proviso that when $R^1$ is methyl $R^3$ is not selected from the group of benzyl, hydroxyethyl and methoxymethyl.

Where reference is made herein to a group comprising an alkyl, alkenyl or alkynyl moiety it will be understood that said moiety may be a straight or branched chain moiety, for example, the group $C_1$ to $C_{18}$ alkyl includes straight and branched chain alkyl of 1 to 18 carbon atoms and the group $C_1$ to $C_9$ alkoxy includes groups wherein the alkyl portion of the alkoxy group is straight or branched chain of from 1 to 9 carbon atoms.

In compounds of formula I, as hereinbefore described the substituents $R^1$ and/or $R^3$ may be a polymer of one or more of the monomers selected from ethylene glycol, propylene glycol and $C_2$ to $C_4$ alkenes and derivatives thereof. Examples of the derivatives may include derivatives comprising at least one group of formula X1 (a) or X1 (b)

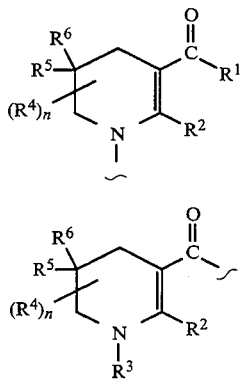

wherein $R^1$, $R^2$, $R^3$, $R^4$, $R^5$, $R^6$ and n are as hereinbefore defined. When the polymer is a polymer of ethylene glycol or propylene glycol examples of derivatives thereof may include ethers formed by a bond of the terminal oxygen with a radical selected from the group of $C_1$ to $C_6$ alkyl, phenyl, benzyl, and the groups phenyl and benzyl substituted in the benzene ring with $C_1$ to $C_9$ alkyl. Preferably the polymers contain in the range of from 3 to 18 monomeric units.

Preferably in the compounds of the invention of formula I $R^1$ is selected from $C_1$ to $C_{18}$ alkyl; $C_2$ to $C_9$ alkyl substituted with a substituent selected from the group consisting of hydroxy, amino, $C_1$ to $C_9$ alkoxy, $C_1$ to $C_9$ alkanoyl and ($C_1$ to $C_9$ alkoxy)carbonyl; $C_1$ to $C_{18}$ alkenyl; cyclohexyl; phenyl; benzyl; the groups phenyl and benzyl said groups being substituted in the benzene ring with a substituent selected from the group of $C_1$ to $C_9$ alkyl, $C_2$ to $C_9$ alkenyl, $C_1$ to $C_9$ alkoxy, $C_1$ to $C_9$ alkanoyl and ($C_1$ to $C_9$ alkoxy)carbonyl; and wherein $R^1$ may optionally link together with $R^2$ by the a bridging group of formula $-CH_2(R^7R^8C)CH_2-$ wherein $R^7$ and $R^8$ are independently selected from hydrogen and $C_1$ to $C_6$ alkyl;

$R^3$ is selected from $C_2$ to $C_{18}$ alkyl; $C_1$ to $C_9$ alkyl substituted with a substituent selected from the group consisting of hydroxy, amino, $C_1$ to $C_9$ alkoxy and $C_1$ to $C_9$ alkanoyl; $C_2$ to $C_{18}$ alkenyl; cyclohexyl; phenyl; benzyl; benzoyl; the groups phenyl, benzyl and benzoyl said groups being substituted in the benzene ring with a substituent selected from the group of $C_1$ to $C_9$ alkyl, $C_2$ to $C_9$ alkenyl, $C_1$ to $C_9$ alkoxy, $C_1$ to $C_9$ alkanoyl and ($C_1$ to $C_9$ alkoxy)carbonyl; $C_3$ to $C_{18}$ alkanoyl; and $C_2$ to $C_{18}$ alkanoyl substituted with phenyl;

$R^2$ is selected from hydrogen and $C_1$ to $C_6$ alkyl; and wherein $R^2$ may link together with $R^1$ to form a carbocyclic ring by the bridging group of formula $-CH_2(R^7R^8C)CH_2-$ wherein $R^7$ and $R^8$ are independently selected from hydrogen and $C_1$ to $C_6$ alkyl;

$R^4$ is $C_1$ to $C_6$ alkyl;

n is from 0 to 4; and $R^5$ and $R^6$ are independently selected from hydrogen; the group of formula III

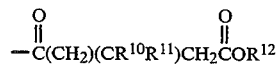

wherein $R^{10}$, $R^{11}$ and $R^{12}$ are independently selected from $C_1$ to $C_4$ alkyl and hydrogen; and wherein $R^5$ and $R^6$ may form a spiro-carbocyclic ring by the bridging group of formula II (a)

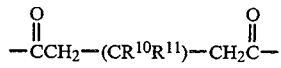

wherein $R^{10}$ and $R^{11}$ are independently selected from hydrogen and $C_1$ to $C_4$ alkyl.

Preferably wherein one of $R^5$ and $R^6$ is the group of formula III then the other is hydrogen.

More preferably in compounds of the invention:

$R^1$ is selected from $C_1$ to $C_{18}$ alkyl; $C_1$ to $C_6$ alkyl substituted with a substituent selected from $C_1$ to $C_6$ alkanoyl and ($C_1$ to $C_6$ alkoxy)carbonyl; $C_1$ to $C_{18}$ alkenyl; phenyl; and benzyl;

$R^2$ is selected from hydrogen and $C_1$ to $C_4$ alkyl and wherein $R^1$ and $R^2$ may form a carbocyclic ring by the bridging group of formula

wherein $R^7$ and $R^8$ are independently selected from hydrogen and $C_1$ to $C_4$ alkyl. $R^3$ is selected from $C_2$ to $C_{18}$ alkyl; $C_1$ to $C_9$ alkyl substituted with a substituent selected from the group consisting of hydroxy and $C_1$ to $C_9$ alkoxy; $C_1$ to $C_{18}$ alkenyl; benzoyl; benzyl; benzoyl substituted with a substituent selected from $C_1$ to $C_6$ alkyl and $C_1$ to $C_6$ alkoxy; and $C_3$ to $C_9$ alkanoyl;

$R^4$ is $C_1$ to $C_4$ alkyl;

n is from 0 to 3; and $R^5$ and $R^6$ are selected such that they comply with one of the possibilities selected from the group consisting of (i) $R^5$ and $R^6$ are independently selected from hydrogen and $C_1$ to $C_4$ alkyl; (ii) one of $R^5$ and $R^6$ is hydrogen and the other is a group of formula III

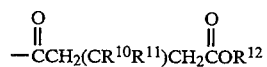

wherein $R^{10}$, $R^{11}$ and $R^{12}$ are independently selected from hydrogen and $C_1$ to $C_4$ alkyl; and (iii) the group wherein $R^5$ and $R^6$ form a spiro carbocyclic ring by the diradical group of formula IIa

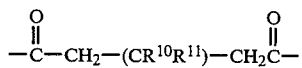

wherein $R^{10}$ to $R^{11}$ are independently selected from hydrogen and $C_1$ to $C_4$ alkyl.

Even more preferably compound of the invention are compounds of formula I wherein:

$R^1$ is $C_1$ to $C_9$ alkyl;
$R^2$ is selected from hydrogen and $C_1$ to $C_4$ alkyl; and wherein $R^1$ and $R^2$ may form a carbocyclic ring by the bridging group of formula

wherein $R^8$ and $R^9$ are methyl;
$R^3$ is selected from $C_2$ to $C_9$ alkyl, $C_2$ to $C_9$ alkenyl; $C_1$ to $C_9$ alkyl substituted with a substituent selected from hydroxy, phenyl and $C_1$ to $C_6$ alkoxy; benzoyl; benzoyl substituted with a substituent selected from the group consisting of $C_1$ to $C_6$ alkyl and $C_1$ to $C_6$ alkoxy, and $C_1$ to $C_9$ alkanoyl;
$R^4$ is selected from $C_1$ to $C_4$ alkyl;
n is from 0 to 3;
$R^5$ and $R^6$ are selected such that they comply with one of the possibilities selected from the group consisting of (i) $R^5$ and $R^6$ are independently selected from hydrogen and $C_1$ to $C_4$ alkyl; (ii) one of $R^5$ and $R^6$ is hydrogen and the other is a group of formula III

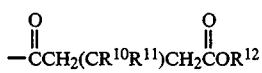

wherein $R^{10}$ and $R^{11}$ are methyl and $R^{12}$ is hydrogen or $C_1$ to $C_4$ alkyl; and (iii) the group wherein $R^5$ and $R^6$ form a spiro carbocyclic ring by the diradical group of formula II a

wherein $R^{10}$ and $R^{11}$ are methyl. Preferably when one of $R^5$ and $R^6$ is not hydrogen or $C_1$ to $C_4$ alkyl then n is zero.

In the most preferred compounds of the invention:
$R^1$ is seleted from the group consisting of methyl, ethyl, propyl and 4-methylbutyl; $R^2$ is hydrogen or methyl; and wherein $R^1$ and $R^2$ may form a carbocyclic ring by the bridging group of formula:

wherein $R^7$ and $R^8$ are methyl;
$R^3$ is selected from the group consisting of: $C_1$ to $C_9$ alkyl such as
propyl, butyl, 1-methylethyl, 1-ethylpropyl, 2-methylbutyl, 3-methylbutyl, hexyl, 2-ethylhexyl, 1-methylpentyl, 1,1-dimethylbutyl, octyl, 1-methylheptyl and 3-methyl-2-butenyl;
2-phenylethyl; benzoyl, 3-methoxybenzoyl; 4-butylbenzoyl; propanoyl; benzyl; and cyclohexyl;
$R^4$ is methyl;
n is chosen from 0 to 3 and is conveniently zero.

$R^5$ and $R^6$ are selected such that they comply with one of the possibilities selected from the group consisting of (i) $R^5$ and $R^6$ are independently selected from hydrogen and methyl; (ii) one of $R^5$ and $R^6$ is hydrogen and the other is a group of formula III

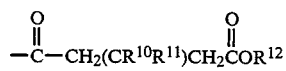

wherein $R^{10}$ and $R^{11}$ are methyl and $R_{12}$ is ethyl; and (iii) the group wherein $R^5$ and $R^6$ form a spiro carbocyclic ring by the diradical group of formula IIa.

wherein $R^{10}$ and $R^{11}$ are methyl.

One group of compounds of the invention which may be used in preparation of sunscreen compositions include compounds of formula Ia

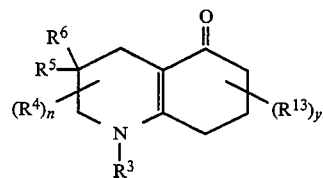

wherein
$R^3$, $R^4$, $R^5$ and $R^6$ are as hereinbefore defined in relation to compounds of the invention, $R^{13}$ is $C_1$ to $C_4$ alkyl and y is from 0 to 3.

Preferrred compounds of formula Ia include compounds of formula I (a) (i)

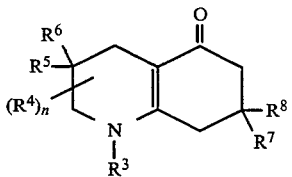

wherein $R^3$, $R^4$, $R^5$, $R^6$, $R^7$, $R^8$ and n are as hereinbefore defined.

Included in the more preferred compounds of the invention of formula I

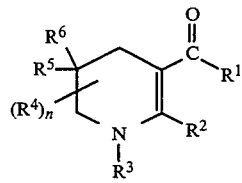

are compounds where $R^5$ and $R^6$ are independently selected from hydrogen, $C_1$ to $C_6$ alkyl and $C_1$ to $C_6$ alkoxy, preferably from hydrogen and $C_1$ to $C_6$ alkyl; more preferably from hydrogen and $C_1$ to $C_4$ alkyl such as methyl; and $R^1$, $R^2$, $R^3$, $R^4$ and n are as hereinbefore defined.

For example, such compound include compounds wherein
$R^1$ is selected from the group consisting of methyl, ethyl, propyl, 3-methylbutyl;
$R^2$ is hydrogen;

$R^3$ is selected from the group consisting of propyl, 1-methylethyl, butyl, 3-methylbutyl, 2-ethylhexyl and 3-methyl-2-butenyl;

n is 0; and $R^5$ and $R^6$ are hydrogen.

The compounds of formula I (a) (i) include such compounds wherein $R^5$ and $R^6$ are hydrogen and $R^3$ is as hereinbefore defined and n is 0, that is the compounds of formula I(a)(ii)

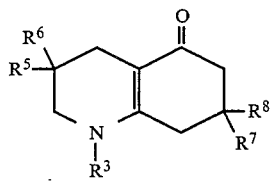

I(a)(ii)

wherein $R^7$ and $R^8$ are as hereinbefore defined.

When in the compounds of formula I(a) $R^5$ and $R^6$ comprise the groups of formula III or formula IIa it is preferred that $R^7$ is identical with the group $R^{10}$ and $R^8$ is identical with the group $R^{11}$.

Specific examples of compounds embraced by the invention include.

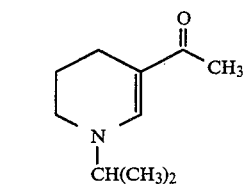 (1)

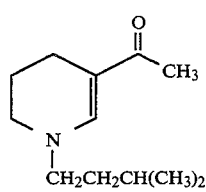 (3)

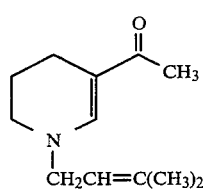 (4)

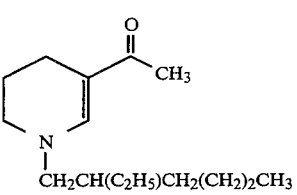 (5)

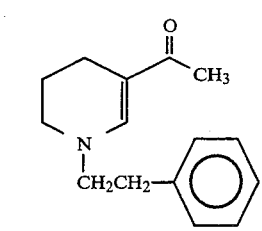 (6)

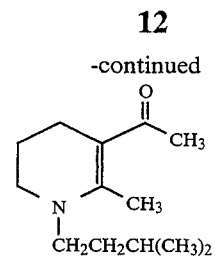 (9)

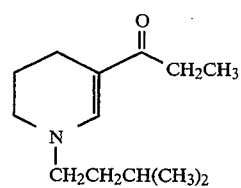 (11)

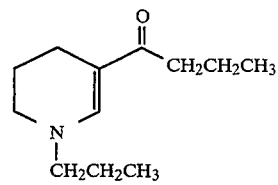 (12)

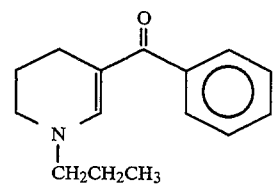 (16)

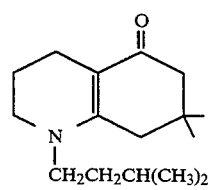 (18)

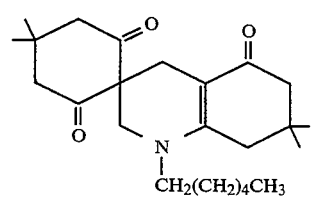 (24)

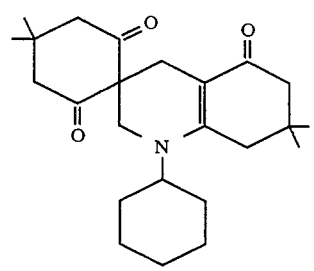 (25)

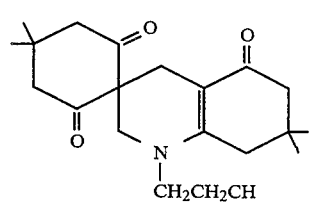 (29)

-continued

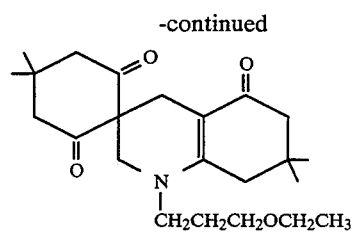
(32)

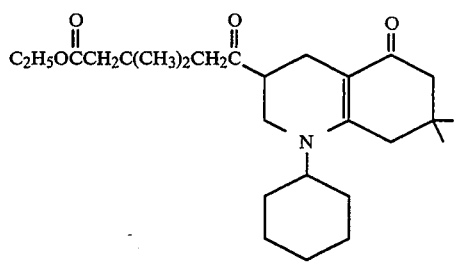
(36)

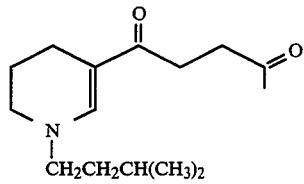
(38)

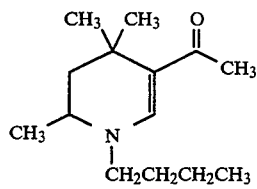
(39)

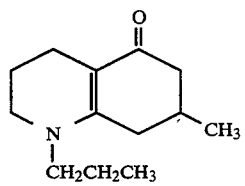
(40)

The compounds of formula I may be prepared by a variety of methods and in a further aspect of the invention there is provided methods for the preparation of compounds of the invention of formula I.

The compounds may generally be derived via a suitable tetrahydropyridine compound of formula IV or via a pyridine derivative of formula V (wherein A are independently selected from hydrogen and $R^4$).

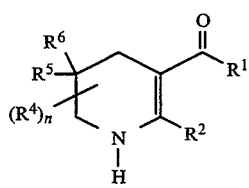
IV

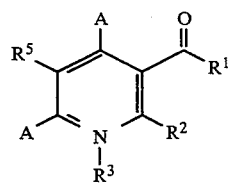
V

The preparation of the compound of formula I from the pyridine derivative of formula V may be carried out by reduction of the compound of formula V for example using hydrogen in the presence of a catalyst (such as palladium on charcoal catalyst) to give a compound of the invention of formula I(c).

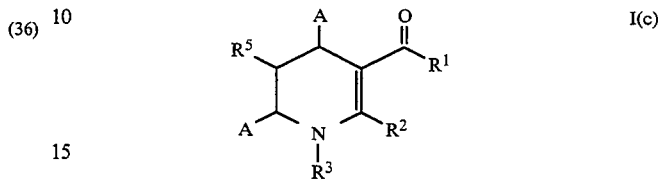
I(c)

The pyridine derivative of formula V may be prepared from the compound of formula VII (wherein A are independently selected from hydrogen and $R^4$) reaction thereof with the compound of formula VI (wherein L is a leaving group).

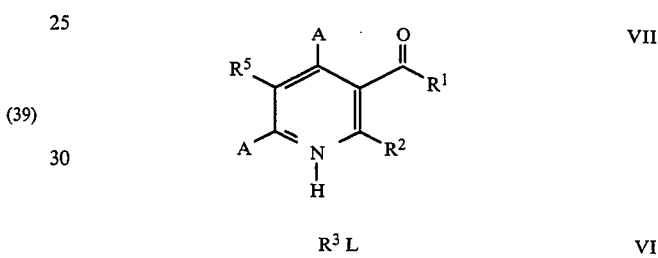
VII $R^3 L$      VI

The preparation of a compound of formula I from the compound of formula IV may be carried out by
reacting the compound of formula IV, preferably in the presence of a base, with a compound of formula VI wherein L is a leaving group.

The compound of formula IV having the specific formula IVa may be prepared by reduction of the pyridine of formula VII, for example using hydrogen in the presence of a catalyst such as palladium on charcoal.

Alternatively the compound of formula IV (having the specific formula IVb) may be prepared by chemical reduction of the compound of formula VIII

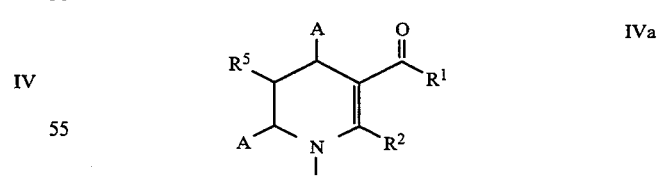
IVa

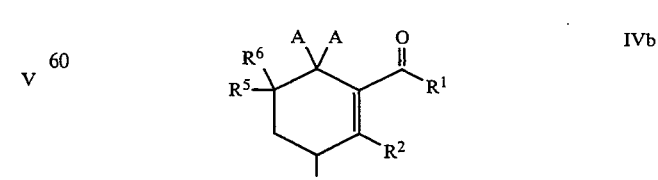
IVb wherein A which may be the same or different is chosen from hydrogen or $R^4$ as hereinbefore defined.

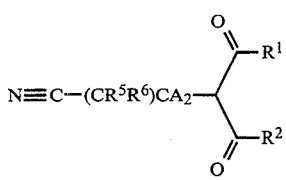

VIII (A is independently selected from hydrogen and R⁴).

In compound of formula VI the leaving group (L) may be chosen by those skilled in the art. Examples of leaving groups include chloride, bromide, iodide, sulfate, nitrate, methylsulfate, ethylsulfate, tetrafluoroborate, hexafluorophosphate, hexafluoroantiminate, methanesulfonate, fluorosulfonate, fluoromethanesulfonate and trifluoromethanesulfonate.

An alternative method of preparation of the compound of formula IV may involve reaction of the compound of formula XII with a compound of formula XIII in the presence of a base such as an amine to give the compound of formula XIV and hydrogenation of the compound of formula XIV to give the compound of formula IV(c) which may be converted as herein before described to a compound of the invention of formula I having the specific formula I(b).

A preferred example of this alternative method is the reaction of the compound of XIII with mesityl oxide to give the compound of formula IV which has the formula XV which may be utilised in providing compounds of formula I having a 4,4,6-trimethyl substitution in the tetrahydro pyridine ring, for example, the compound methyl 1-butyl-4,4,6-trimethyl-1,4,5,6-tetrahydro-3-pyridyl ketone.

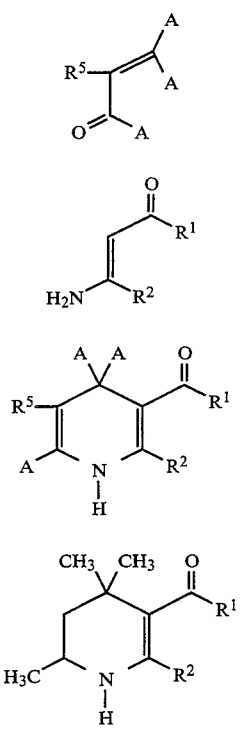

XII

XIII

XIV

XV

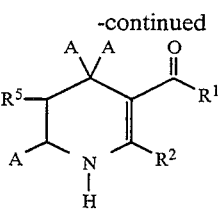

IV(c)

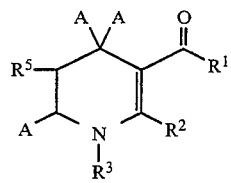

Ib (A is independently selected from hydrogen and R⁴)

A similar scheme may be used for more direct preparation of the compound of formula I by reaction of the compound of formula XII with a compound of formula XVI followed by hydrogenation of the intermediate of formula XVII to give a compound of the invention of formula I(b).

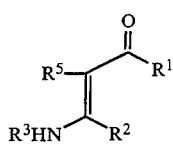

XVI

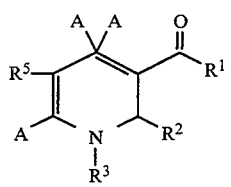

XVII

There is further provided a process for preparation of a compound of formula I (a)(iii)

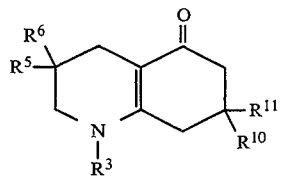

I(a)(iii)

wherein $R^5$ and $R^6$ together from the spiro carbocyclic ring by the diradical group of formula III a

IIa or one of $R^5$ and $R^6$ is hydrogen and the other is the group of formula III

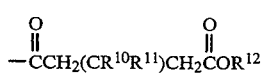

III and $R^3$, $R^{10}$, $R^{11}$ and $R^{12}$ are as hereinbefore defined; which process comprises reacting a compound of formula IX with formaldehyde

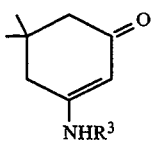

in presence of an acid to give a compound of the invention of formula I (a)(iii) wherein $R^5$ and $R^6$ from said spiro carbocyclic ring of formula IIa; and optionally reacting the spiro carbocyclic moiety with a base of formula X.

MOR$^{12}$

X, wherein M is an alkali metal cation, to provide a compound of the invention of formula I (a) (iii).

TABLE 1a

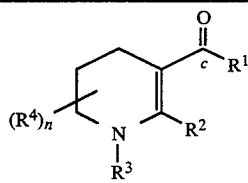

| Compound No. | $R^1$ | $R^2$ | $R^3$ | $R^4$ |
|---|---|---|---|---|
| 1 | CH$_3$ | H | —CH(CH$_3$)$_2$ | — |
| 2 | CH$_3$ | H | n-C$_3$H$_7$ | — |
| 3 | CH$_3$ | H | —CH$_2$CH$_2$CH(CH$_3$)$_2$ | — |
| 4 | CH$_3$ | H | —CH$_2$CH=C(CH$_3$)$_2$ | — |
| 5 | CH$_3$ | H | —CH$_2$CH(C$_2$H$_5$)CH$_2$(C$_2$)$_2$CH$_3$ | — |
| 6 | CH$_3$ | H | —C$_2$H$_4$C$_6$H$_5$ | — |
| 7 | CH$_3$ | H | —COC$_6$H$_5$ | — |
| 9 | CH$_3$ | CH$_3$ | —CH$_2$CH$_2$CH(CH$_3$)$_2$ | — |
| 10 | C$_2$H$_5$ | H | n-C$_4$H$_9$ | — |
| 11 | C$_2$H$_5$ | H | CH$_2$CH$_2$CH(CH$_3$)$_2$ | — |
| 12 | n-C$_3$H$_7$ | H | n-C$_3$H$_7$ | — |
| 13 | n-C$_3$H$_7$ | H | n-C$_4$H$_9$ | — |
| 14 | n-C$_3$H$_7$ | H | —CH$_2$CH$_2$CH(CH$_3$)$_2$ | — |
| 15 | —CH$_2$(CH$_2$)$_2$CH(CH$_3$)$_2$ | H | n-C$_3$H$_7$ | — |
| 16 | C$_6$H$_5$ | H | n-C$_3$H$_7$ | — |
| 38 | CH$_2$CH$_2$C(O)CH$_3$ | H | CH$_2$CH$_2$CH(CH$_3$)$_2$ | — |
| 39 | CH$_3$ | H | C$_4$H$_9$ | 4,4,6-(CH$_3$)$_3$ |

TABLE 1b

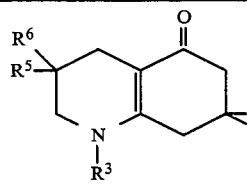

| Compound No | $R^3$ | $R^5, R^6$ |
|---|---|---|
| 17 | n-C$_3$H$_7$ | H, H |
| 18 | —CH$_2$CH$_2$CH(CH$_3$)$_2$ | H, H |
| 19 | —CCO$_6$H$_5$ | H, H |
| 20 | —COC$_6$H$_4$(3)OCH$_3$ | H, H |
| 21 | —COC$_6$H$_4$(3)OCH$_3$ | H, H |
| 22 | —COC$_6$H$_4$(4)-n-C$_4$H$_9$ | H, H |
| 23 | n-C$_6$H$_{14}$ | a |
| 25 | b | a |
| 26 | —CH$_2$C$_6$H$_5$ | a |

TABLE 1b-continued

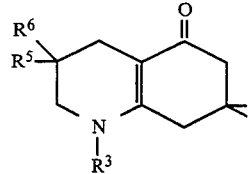

| Compound No | $R^3$ | $R^5, R^6$ |
|---|---|---|
| 27 | n-C$_8$H$_{18}$ | a |
| 28 | —CH$_2$CH(CH$_3$)CH$_2$CH$_3$ | a |
| 29 | —CH$_2$CH$_2$OH | a |
| 30 | —CH$_2$CH(CH$_3$)CH$_2$CH$_3$ | a |
| 31 | —CH(C$_2$H$_5$)CH$_2$CH$_3$ | a |
| 32 | —CH$_2$CH$_2$CH$_2$OC$_2$H$_5$ | a |
| 33 | —CH(CH$_3$)CH$_2$(CH$_2$)$_3$CH$_3$ | a |
| 34 | —CH(CH$_3$)CH$_2$(CH$_2$)$_4$CH$_3$ | a |
| 35 | —C(CH$_3$)$_2$CH$_2$CH$_2$CH$_3$ | a |
| 36 | b | H, C |

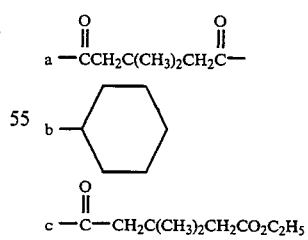

a —CCH$_2$C(CH$_3$)$_2$CH$_2$C— b (cyclohexyl)

c —C—CH$_2$C(CH$_3$)$_2$CH$_2$CO$_2$C$_2$H$_5$

In a further embodiment of the invention, there is provided a method of screening a surface from ultraviolet radiation, the method comprising applying to the surface a composition comprising a compound of formula I as hereinbefore described.

The compositions of the present invention are particularly useful for protection of human skin against harmful effects of sunlight. Human skin is well known to be sensitive to sunlight containing radiation of wavelengths between about 270 nm and 400 nm.

The UV-B region of ultra violet radiation (290–320 nm) has long been known to cause damage to skin but more recently concern has been expressed over the effect of UV-A radiation (above 320 nm).

Compositions of the present invention may be prepared comprising one or more compounds of formula I and may provide screening in the UV-A region, the UV-B region or in both of these regions.

Consequently, in one embodiment of the invention there is provided a method of protecting skin from ultra-violet radiation, the method comprising applying to the surface of the skin a composition as hereinbefore described.

A specific example of a sunscreen formulation which may be used in preparation of compositions of the present invention includes the following

| Sunscreen lotion composition | % w/w |
| --- | --- |
| Methyl para-hydroxy benzoate | 0.25 |
| Propyl para-hydroxy benzoate | 0.10 |
| Cetyl/Stearyl 2-Ethylhexanoate | 2.00 |
| "CARBOMER" 491 thickener (cross linked acrylic acid polymer) | 0.45 |
| Phenyl trimethicone | 1.00 |
| Stearic Acid | 3.00 |
| Sodium Hydroxide | 0.15 |
| Phenoxyethanol | 0.30 |
| Isopropyl Isostearate | 5.00 |
| Antioxidant (BHA, BHT, ascorbates, tocopherols) | 0.08 |
| Glyceryl Monostearate & PEG 100 Stearate | 1.00 |
| Fragrance | 0.10 |
| Sunscreen Compound | 6.00 |
| Disodium EDTA | 0.05 |
| Treated water | 80.52 |

("CARBOMER" is a trade mark)

The invention is now illustrated by, but in no way limited to, the following examples.

EXAMPLE 1

Methyl 1-(1-methylethyl)-1,4,5,6-tetrahydro-3-pyridyl ketone (1)

a) 3-acetyl-1,4,5,6-tetrahydropyridine was prepared by hydrogenation of 3-acetyl pyridine in the presence of palladium on carbon according to the method of Freifelder, *J. Org. Chem.* 29, 2895 (1964).

b) 3-acetyl-1,4,5,6-tetrahydropyridine (20.0 g, 0.16 mole) was added under nitrogen to a mixture of sodium hydride (5.76 g, 0.24 mole) and dry dimethylformamide (50 ml) stirring at 0° C. and stirring was continued for 15 minutes. 2-Bromopropane (21.5 g, 0.175 mole) was then added dropwise over 15 min, stirring continued for a further hour at 0° C. then overnight at room temperature. The reaction mixture was cautiously added to iced water (100 g) under nitrogen and extracted with diethyl ether (3×100 ml). The combined organic phase was extracted with water (150 ml), dried over magnesium sulphate, concentrated under reduced pressure to give methyl 1-(1-methylethyl)-1,4,5,6-tetrahydro-3-pyridyl ketone (1). The product was distilled as a pale yellow oil (b.pt 97°–98° C./0.5 mm Hg).

EXAMPLE 2

Methyl 1-propyl-1,4,5,6-tetrahydro-3-pyridyl ketone (2)

a) Methyl 1-propyl-1,4,5,6-tetrahydro-3-pyridyl ketone was prepared from 3-acetyl-1,4,5,6-tetrahydropyridine and 1-bromopropane according to the procedure of Part b) of Example 1. The product distilled as a pale yellow (b.pt 98°–100° C./0.5 mm Hg).

EXAMPLE 3

Methyl 1-(3-methylbutyl)-1,4,5,6-tetrahydro-3-pyridyl ketone (3)

Methyl 1-(3-methylbutyl)-1,4,5,6-tetrahydro-3-pyridyl ketone was prepared from 3-acetyl-1,4,5,6-tetrahydropyridine and 1-bromo-3-methylbutane according to the procedure of Part b) of Example 1. The product distilled as a pale yellow oil (b.pt. 103°–106° C./0.1 mm Hg).

EXAMPLE 4

Methyl 1-(3-methyl-2-butenyl)-1,4,5,6-tetrahydro-3-pyridyl ketone (4)

a) A mixture of 3-acetylpyridine (12.1 g, 0.1 mole) and 1-bromo-3-methyl-2-butene (22.3 g, 0.15 mole) was stirred at room temperature under nitrogen overnight. The mixture was diluted with diethyl ether (25 ml) and the cream coloured crystalline solid, 1-(3-methyl-2-butenyl)-3-acetyl pyridinium bromide, was filtered off under nitrogen.

b) 1-(3-methyl-2-butenyl)-3-acetyl-pyridinium bromide (27.0 g, 0.1 mole) and triethylamine (10.1 g, 0.1 mole) in ethyl alcohol (50 ml) over 5% palladium on carbon (5 g) was hydrogenated at room temperature and pressure until two molar equivalents of hydrogen was taken up. The catalyst was removed by filtration and the filtrate concentrated at reduced pressure. The semi-solid residue was diluted with diethyl ether (75 ml), the solid removed by filtration and the filtrate concentrated under reduced pressure to leave a pale oil which solidified on standing. Recrystallisation from ethanol/water gave the product, methyl 1-(3-methylbutenyl)-1,4,5,6-tetrahydro-3-pyridyl ketone (4) as a pale yellow crystalline solid m.p. 76°–78° C.

EXAMPLE 5

Methyl 1-(2-ethylhexyl)-1,4,5,6-tetrahydro-3-pyridyl ketone (5)

a) 3-acetyl-1,4,5,6-tetrahydropyridine (20.0 g, 0.16 mole) was added under nitrogen to a mixture of sodium hydride (5.76 g, 0.24 mole) and dry tetrahydrofuran (50 ml) stirring at room temperature. After one hour, 1-bromo-2-ethyl hexane (33.8 g, 0.175 mole) was added dropwise over 15 minutes and the mixture stirred overnight at room temperature. The reaction mixture was cautiously added to iced water (100 g) under nitrogen and extracted with diethyl ether (3×100 ml). The combined organic phase was dried over magnesium sulphate, concentrated under reduced pressure and the residue distilled to give methyl 1-(2-ethylhexyl)-1,4,5,6-tetrahydro-3-pyridyl ketone (5) as a pale yellow oil (b.pt 140°–142° C./0.1 mm Hg).

EXAMPLE 6

Methyl 1-(2-phenylethyl)-1,4,5,6-tetrahydro-3-pyridyl ketone (6)

a) A mixture of 3-acetyl pyridine (12.1 g, 0.1 mole) and (2-bromoethyl)benzene (37.0 g, 0.2 mole) was heated at 100° C. under nitrogen for four hours. After cooling, the mixture was diluted with diethyl ether (25 ml) and the pale brown crystalline solid, 1-(2-phenyl ethyl) -3-acetyl-pyridinium bromide, was filtered off under nitrogen.

b) A solution of 1-(2-phenylethyl)-3-acetylpyridinium bromide (30.6 g, 0.1 mole) and triethylamine (10.1 g, 0.1 mole) in ethyl alcohol (50 mole) over 5% palladium on carbon (5 g) was hydrogenated at room temperature and pressure. Upon cessation of hydrogen uptake, the catalyst was filtered and the filtrate concentrated at reduced pressure. The semi-solid filtered and the filtrate concentrated under reduced pressure to leave a pale brown oil, methyl 1-(2-phenyl ethyl)-1,4,5,6-tetrahydro-3-pyridyl ketone (6).

EXAMPLE 7

Methyl 1-benzoyl-1,4,5,6-tetrahydro-3-pyridyl ketone (7)

a) Methyl 1-benzoyl-1,4,5,6-tetrahydro-3-pyridyl ketone was prepared from 3-acetyl-1,4,5,6-tetrahydropyridine and benzoyl chloride according to the procedure of Part b) of Example 1. The product was recrystallised from ethanol/water m.pt. 93°–95° C.

EXAMPLE 8 AND EXAMPLE 9

Methyl 1-(3-methylbutyl)-2-methyl-1,4,5,6-tetrahydro-3-pyridyl ketone (9)

EXAMPLE 8 a) 4,4-Diacetylbutyronitrile was prepared by addition of acrylonitrile to the sodium salt of acetyl acetone according to the procedure of Johnson et al, *J.Chem.-Soc (C), 1969, 176.* b) A solution of 4,4-diacetylbutyronitrile (15.3 g, 0.1 mole) in ethyl alcohol (50 ml) over Raney nickel (2 g) was hydrogenated at room temperature and three atmospheres pressure. After hydrogen uptake had ceased, the catalyst was filtered off and the filtrate concentrated under reduced pressure to give 3-acetyl-2-methyl-1,4,5,6-tetrahydropyridine.

EXAMPLE 9

Methyl 1-(3-methylbutyl)-2-methyl-1,4,5,6-tetrahydro-3-pyridyl ketone was prepared from 3-acetyl-2-methyl, 1,4,5,6-tetrahydro- pyridine and 1-bromo-3-methylbutene according to the procedure of Part b) of Example 1.

EXAMPLE 10

Ethyl 1-butyl-1,4,5,6-tetrahydro-3-pyridyl ketone (10)

a) A mixture of ethyl nicotinate (15.1 g, 0.1 mole), ethyl propionate (15.3 g, 0.15 mole) and sodium ethoxide (10.2 g, 0.15 mole) was stirred and heated under nitrogen at 100° C. for five hours. After cooling, the mixture was diluted with water (150 ml) extracted with diethyl ether (50 ml) and the aqueous layer made acidic to pH 1 with concentrated hydrochloric acid (50 ml). The aqueous layer was heated at 90° C. for two hours, cooled, made alkaline with solid potassium carbonate and extracted with diethyl ether (3×75 ml). The dried (magnesium sulphate) organic layer was concentrated and distilled to give ethyl 3-pyridyl ketone (b.pt 97°–99°/14 mm Hg).

b) Ethyl 3-pyridyl ketone was reacted with 1-bromobutane according to the procedure of Para a) of Example 6 to give 1-butyl(3-pyridinium bromide as a tan coloured crystalline solid.

c) 1-Butyl-3-propionyl pyridinium bromide was hydrogenated according to the procedure described in Para b) at Example 6 to give ethyl 1-butyl-1,4,5,6-tetrahydro-3-pyridyl ketone (10). The product was distilled as a pale yellow oil (b.pt. 108°–109° C./0.1 mm Hg).

EXAMPLE 11

Ethyl 1-(3-methylbutyl)-1,4,5,6-tetrahydro-3-pyridyl ketone (11)

a) Ethyl 3-pyridyl ketone was reacted with 1-bromo-3-methylbutane according to the procedure of Parb a) of Example 6 to give 1-(3-methylbutyl)-3-propionyl pyridinium bromide as a pale brown crystalline solid.

b) 1-(3-Methylbutyl)-3-propionyl pyridium bromide was hydrogenated according to the procedure of Parb b) of Example 6 to give ethyl 1-(-3-methylbutyl-1,4,5,6-tetrahydro-3-pyridyl ketone. The product was distilled as a pale yellow oil (b.pt. 111°–112° C./0.02 mm Hg).

EXAMPLE 12

Propyl 1-propyl-1,4,5,6-tetrahydro-3-pyridyl ketone (12)

a) A mixture of ethyl nicotinate (15.1 g, 0.1 mole), ethyl butyrate (17.4 g, 0.15 mole) and sodium ethoxide (10.2 g, 0.15 mole) was stirred and heated under nitrogen at 100° C. for five hours. After cooling, the mixture was diluted with water (150 ml), extracted with diethyl ether (50 ml) and the aqueous layer made acidic to pH1 with concentrated hydrochloric acid (50 ml). The aqueous layer was heated at 90° C. for 2 hours, cooled, and made alkaline with solid potassium carbonate and extracted with diethyl ether (3×75 ml). The dried (magnesium sulphate) organic layer was concentrated and distilled to give propyl 3-pyridyl ketone (b.pt. 118°–120° C./14 mm Hg).

b) Propyl 3-pyridyl ketone was reacted with 1-bromo-2-propene according to the procedure of Part a) of Example 4 to give 1-(2-propenyl)-3-butyryl pyridium bromide as a cream coloured crystalline solid.

c) 1-(2-Propenyl)-3-butyryl pyridinium bromide was hydrogenated according to the procedure described in Part b) of Example 6 to give propyl 1-propyl-1,4,5,6-tetrahydro-3-pyridyl ketone. The product was distilled as a pale yellow oil (b.pt 150°–153° C./0.3 mm Hg)

EXAMPLE 13

Propyl 1-butyl-1,4,5,6-tetrahydro-3-pyridyl ketone (13)

a) Propyl 3-pyridyl ketone was reacted with 1-bromobutane according to the procedure of Part a) of Example 6 to give 1-butyl-3-butyryl pyridinium bromide as a tan coloured crystalline solid.

b) 1-Butyl-3-butyryl pyridinium bromide was hydrogenated according to the procedure described in Part b) of Example 6 to give propyl 1-butyl-1-4,5,6-tetrahydro-3-pyridyl ketone (13). The product was distilled as a pale yellow oil (b.pt. 120°–124° C./0.02 mm Hg).

EXAMPLE 14

Propyl 1-(3-methylbutyl)-1,4,5,6-tetrahydro-3-pyridyl ketone (14)

a) Propyl 3-pyridyl ketone was reacted with 1-chloro-3-methyl-2-butene according to the procedure of Part a) of Example 4 to give 1-(3-methyl-2-butenyl)-3-butyryl pyridinium chloride as a cream coloured crystalline solid.

b) 1-(3-Methyl-2-butenyl)-3-butyryl pyridinium chloride was hydrogenated according to the procedure described in Part b) of Example 6 to give propyl 1-(3-methylbutyl)-1,4,5,6-tetrahydro-3-pyridyl ketone (14). The product was distilled as a pale yellow oil (b.pt. 126°–129° C./0.02 mm Hg).

EXAMPLE 15

4-Methylpentanyl 1-propyl-1,4,5,6-tetrahydro-3-pyridyl ketone (15)

a) A solution of 3-cyanopyridine (26.0 g, 0.25 mole) in dry diethyl ether (200 ml) was added dropwise over the hour to the Grignard reagent prepared from 1-bromo-3-methyl butane (40.7 g, 0.27 mole) and magensium (6.8 g, 0.26 mole) in dry diethyl ether (50 ml) under nitrogen. The mixture was heated at 35° C. for eight hours, cooled to room temperature, and diluted with cold saturated aqueous ammonium chloride solution(200 ml) followed by concentrated hydrochloric acid (50 ml). The mixture was stirred for five hours, the ether layer separated, and the aqeuous layer boiled for two hours. The aqueous layer was neutralised to pH9 with aqueous sodium hydroxide solution and extracted with diethyl ether (3×100 ml). The organic phase was dried (magnesium sulphate), concentrated under reduced pressure and distilled to give 3-methylbutyl 3-pyridyl ketone.

b) 3-Methylbutyl 3-pyridyl ketone was reacted with 1-bromo-2-propene according to the procedure of Part a) of Example 4 to give 1-(2-propenyl)-3-(4-methyl)valeryl pyridinium bromide as a tan coloured crystalline solid.

c) 1-(2-Propenyl)-3-(4-methyl)valeryl pyridinium bromide was hydrogenated according to the procedure of Part b) of Example 6 to give 4-methylpentanyl 1-propyl-1,4,5,6-tetrahydro-3-pyridyl ketone (15) as a yellow oil.

EXAMPLE 16

Phenyl 1-propyl-1,4,5,6-tetrahydro-3-pyridyl ketone (16)

a) 3-Benzoyl pyridine was reacted with 1-bromo-2-propene according to the procedure of Part a) of Example 4 to give 1-(2-propenyl)-3-benzoyl pyridinium bromide as a tan coloured crystalline solid.

b) 1-(2-Propenyl)-3-benzoyl pyridinium bromide was hydrogenated according to the procedure of Part b) of Example 6 to give phenyl 1-propyl-1,4,5,6-tetrahydro-3-pyridyl ketone (10) as a yellow oil.

EXAMPLE 17

7,7-Dimethyl-1,2,3,4,7,8-hexahydro-1-propyl-quinolin-5(6H)-one(17)

a) 7,7-Dimethyl-1,2,3,4,7,8-hexahydro-quinolin-5 (6H)-one [prepared by the method of Grob and Kiefer, Helv. Chim Acta., 48 799, (1964)] was reacted with 1-bromopropane according to the procedure of Part (b) of Example 1 to give 7,7-dimethyl-1,2,3,4,7, 8-hexahydro-1-propyl-quinolin-5(6H)-one (17) as an oil.

EXAMPLE 18

7,7-Dimethyl-1,2,3,4,7,8-hexahydro-1-(3-methylbutyl)-quinoline-5(6H)-one(18)

a) 7,7-Dimethyl-1,2,3,4,7,8-hexahydro-quinolin-5(6H)-one was reacted with 1-bromo-3-methylbutane according to the procedures of Part b) of Example 1 to give 7,7-dimethyl-1,2,3,4,7,8-hexahydro-1-(3-methylbutyl)-quinolin-5(6H)-one (18) as a pale yellow oil.

EXAMPLE 19

7,7-Dimethyl-1,2,3,4,7,8-hexahydro-1-benzoyl-quinolin-5(6H)-one(19)

a) 7,7 Dimethyl-1,2,3,4,7,8-hexahydro-quinolin-5(6H)-one was reacted with benzoyl chloride according to the procedure of Part b) of Example 1 to give 7,7-dimethyl-1,2,3,4,7,8-hexahydro-1-benzoyl-quinolin-5(6H)-one(19) as a yellow solid.

EXAMPLE 20

7,7-Dimethyl-1,2,3,4,7,8-hexahydro-1-(3-methoxybenzoyl)-quinolin-5(6H)-one(20)

a) 7,7-Dimethyl-1,2,3,4,7,8-hexahydro-quinolin-5(6H)-one was reacted with 3-methoxybenzoyl chloride according to the procedure of Part b) of Example 1 to give 7,7-dimethyl-1,2,3,4,7,8-hexahydro-1-(3-methoxybenzoyl)-quinolin-5(6H)-one (20) as a pale yellow solid.

EXAMPLE 21

7,7-Dimethyl-1,2,3,4,7,8-hexahydro-1-(4-methoxybenzoyl)-quinoline-5(6H)-one (21)

a) 7,7-Dimethyl-1,2,3,4,7,8-hexahydro-quinoline-5(6H)-one was reacted with 4-methoxybenzoyl chloride according to the procedure of Part b) of Example 1 to give 7,7-dimethyl-1,2,3,4,7,8-hexahydro-1-(4-methoxybenzoyl)-quinoline-5(6H)-one(21) as a yellow waxy solid.

EXAMPLE 22

7,7-Dimethyl-1,2,3,4,7,8-hexahydro-1-(4-butylbenzoyl)-quinolin-5(6H)-one(22)

a) 7,7-Dimethyl-1,2,3,4,7,8-hexahydro-quinoline-5(6H)-one was reacted with 4-butylbenzoyl chloride according to the procedure of Part b) of Example 1 to give 7,7-dimethyl-1,2,3,4,7,8-hexahydro-1-(4-butylbenzoyl)-quinoline-5(6H)-one(22) as a yellow solid.

EXAMPLE 23

Preparation of 1,2,3,4,7,8-hexahydro-1-hexyl-4',4',7,7-tetramethyl-quinoline-3-spirocyclohexane-2',5(6H), c'-trione (23)

a) A solution of 5,5-dimethyl-3-hexylaminocyclohex-2-enone (26.76 g; 0.12 mole), aqueous formaldehyde (37% w/w; 9 ml) and 2N hydrochloric acid (40 ml) was stirred at room temperature for 24h. The reaction was chilled on ice and made basic with 4N NH.OH. The resulting solid was collected by filtration, washed with water (3×100 ml) and dried in vacuo to give 19.2 g (85.3%) of 1,2,3,4,7,8-hexahydro-1-hexyl-4',4',7,7-tetramethylquinoline-3-spirocyclohexane-2',5(6H),6'-trione, m.p. 111.1°–113.0° C.

max 314.0 mm (=27750)

EXAMPLE 24

The reaction solution of Example 23 consisting of 5,5-dimethyl-3-hexylaminocyclohex-2-enone (26.76 g; 0.12 mole), aqueous formaldehyde (37% w/w; 9 ml) and 2N hydrochloric acid (40 ml) was refluxed for 5 h. The reaction mixture was chilled on ice, made basic with 2NNH.OH, extracted into chloroform (3×100 ml) and dried over MgSO₄. Evaporation of the chloroform and crystallisation of the residue from benzene/light petroleum gave 20.6 g (91.6%) of 1,2,3,4,7,8-hexahydro-1-hexyl-4',4',7,7-tetramethylquinoline-3-spirocyclohexane-2',5(6H),6'-trione, m.p. 111.1°–113.0° C.

EXAMPLE 24

PMR (300 MHz; CDCl₃

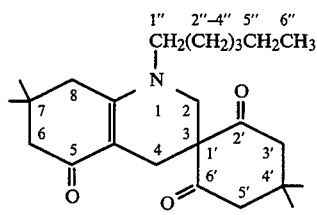

$C_2$ ($H_2$) 3.438 (s;2H) $C_3$, ($H_2$) 2.140 (s;2H)
$C_4$ ($H_2$) 2.883 (s;2H) $C_4$, ($CH_3$)$_2$ 1.318 (m;6H)
$C_6$ ($H_2$) 3.080 (s;1H) $C_5$, ($H_2$) 2.235 (m; 2H)
  3.036 (s;1H)
$C_7$ ($CH_3$)$_2$ 0.916 (s;6H) $C_{1''}$, ($H_2$) 3.331 (t;2H)
$C_8$ ($H_2$) 2.211 (s;1H) $C_{2''}$–$C_{4''}$ ($H_2$)$_3$ 1.318 (m;6H)
  2.258 (s;1H)
  $C_{5''}$ ($H_2$) 1.690 (m;2H)
  $C_{6''}$ ($H_3$) 0.894 (t;3H)

EXAMPLE 25–35

Preparation of 1-substituted-1,2,3,4,7,8-hexahydro-4',4',7,7-tetramethylquinoline-3-spirocyclohexane-2',5(6H),6'-trione derivatives The compound derivatives provided in Example 25–35 of the invention were prepared by the general method described in Example 23 or Example 24 and are listed in Table I where the R³-group is defined as the 1-substituent.

TABLE 1

1-substituted (R³)-1,2,3,4,7,8-hexahydro-4',4',7,7-tetramethylquinoline-3-spirocyclohexane-2',5(6h),6'-trione derivatives

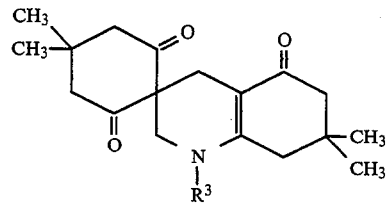

| Example No. | R³ | λmax (mm) (MeOH) | ε(MeOH) | M.P. (°C.) |
|---|---|---|---|---|
| 25 | cyclohexyl | 315.6 | 29230 | 203.1–204.5 |
| 26 | benzyl | 313.0 | 28800 | 180.2–181.6 |
| 27 | n-octyl | 314.4 | 28150 | 150–160/1Torr* |
| 28 | 2-methylbutyl | 313.8 | 27100 | 115.7–116.9 |
| 29 | 2-hydroxyethyl | 317.0 | 27250 | 112.5–113.4 |
| 30 | 2-ethylbutyl | 315.6 | 27600 | 113.8–114.8 |
| 31 | 3-pentyl | 315.6 | 28260 | 119.0–120.0 |
| 32 | 3-ethoxypropyl | 315.4 | 27750 | 167.4–170.0 |
| 33 | 3-heptyl | 314.6 | 28410 | 211.0–212.9 |
| 34 | 2-octyl | 316.2 | 26300 | 160–180/1Torr* |
| 35 | 1,3-dimethylbutyl | 315.2 | 24500 | 109.8–110.8 |

*boiling point (°C./Torr).

EXAMPLE 36

Preparation of ethyl 3,3-dimethyl-5-(1,2,3,4,5,6,7,8-octahydro-1-cyclohexyl-7,7-dimethylquinolin-3-yl-5-oxopentanoate(36)

The compound of Example 36 was prepared by a reverse Dieckmann reaction by the general equation (R³=cyclohexyl):

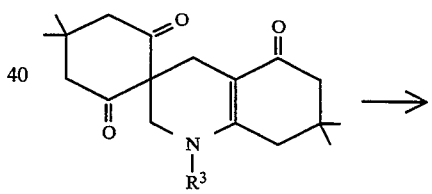

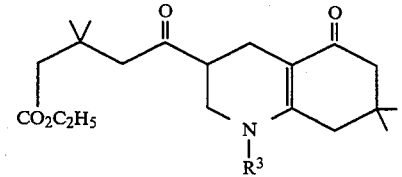

1,2,3,4,7,8-Hexahydro-1-cyclohexyl-4'4',7,7-tetramethylquinoline-3-spirocyclohexane-2',5(6H)6'-trione (Example 25; 6.6 g; 0.0175 mole) was added to ethanolic sodium hydroxide [from sodium (0.9 g)] and ethanol (80 ml)]. The mixture was refluxed for 2h and the ethanol evaporated in vacuo. The residue was treated with ice-cold water (100 ml) and the product extracted into chloroform (3×50 ml). The chloroform layer was dried over MgSO₄ and evaporated to give the crude ester (3.9 g; 54.0% as a pale yellow solid. The product was recrystalised from n-hexane/benzene to give pure ethyl 3,3-dimethyl-5-(1,2,3,4,5,6,7,8-octahydro-1-cyclohexyl-7,7-dimethylquinoline-3-yl)-5-oxopentanoate, m.p. 44°–46° C.

max 318.6 mm, =25,900

EXAMPLE 37

The compounds of Examples 1 to 24 inclusive were characterised by, and can be identified by their 'H nuclear magnetic resonance spectra. The 'H nuclear magnetic resonance spectra for the compounds of Examples 1 to 23 are recorded in Table 2 below

TABLE 2

| Compound No. | Appearance | UV spectra λmax (nm) | log E | 'H N.M.R. δ in ppm (CDCl₃) |
|---|---|---|---|---|
| 1 | pale yellow oil bpt = 97–98° @ 0.5 mm Hg | 312 | 4.47 | 1.20 s 3H<br>1.27 s 3h<br>1.63–1.94 q 2H<br>2.13 s 3H<br>2.22–2.47 q 2H<br>3.01–3.20 t 2H<br>3.33–3.68 Sept.1H<br>7.40 s 1H |
| 2 | pale yellow oil bpt = 98–100° C. @ 0.5 mm Hg | 312 | 4.45 | 0.74–1.05 t 3H<br>1.38–1.96 m 4H<br>2.13 s 3H<br>2.18–2.49 m 2H<br>2.91–3.29 m 4H<br>7.32 s 1H |
| 3 | pale yellow oil bpt = 103–106° C. @ 0.1 mm Hg | 312 | 4.45 | 0.94 d 6H<br>1.40–1.60 m 3H<br>1.60–2.00 m 2H<br>2.10 s 3H<br>2.10–2.40 3H<br>2.10–2.40 q 2H<br>3.00–3.30 q 4H<br>7.30 s 1H |
| 4 | pale yellow solid mpt = 76–78° C. | 312 | 4.46 | 1.68 s 3H<br>1.76 s 3H<br>1.65–1.89 tt 2H<br>2.12 s 3H<br>2.25–2.35 t 2H<br>3.01–3.09 m 2H<br>3.65–3.72 d 2H<br>5.07–5.21 t 1H<br>7.27 s 1H |
| 5 | pale yellow oil bpt = 140–142° C. @ 0.1 mm Hg | 311.8 | 4.53 | 0.75–1.03 t 6H<br>1.03–1.52 m 9H<br>1.52–1.96 m 2H<br>2.12 s 3H<br>2.19–2.44 t 2H<br>2.95–3.20 t 4H<br>7.26 s 1H |
| 6 | yellow oil | 311.5 | 4.38 | 1.60–1.93 t 2H<br>1.99 s 3H<br>2.09–2.39 m 2H<br>2.72–2.97 t 2H<br>3.00–3.24 t 2H<br>3.27–3.54 t 2H<br>7.02 s 1H<br>7.24 s 5H |
| 7 | yellow solid mpt = 93–95° C. | 289 | 4.27 | 1.74–2.03 m 2H<br>2.16 s 3H<br>2.27–2.51 t 2H<br>3.64–3.88 t 2H<br>7.50 s 5H<br>7.88 s 1H |
| 9 | pale yellow oil bpt = 106–109° C. @ 0.1 mm Hg | 318 | 4.45 | 0.90 s 3H<br>0.95 s 3H<br>1.31–1.98 m 5H<br>2.11 s 3H<br>2.22–2.51 m 2H<br>2.41 s 3H<br>3.05–3.36 m 4H |
| 10 | yellow oil bpt = 108–109° C. @ 0.1 mm Hg | 312 | 4.44 | 0.81–1.23 m 6H<br>1.23–1.99 m 6H<br>2.20–2.63 m 4H<br>3.00–3.31 m4H<br>7.32 s 1H |
| 11 | pale yellow oil bpt = 111–112° C. @ 0.02 mmHg | 312 | 4.42 | 0.90–0.96 d 6H<br>1.02–1.20 t 3H<br>1.20–1.62 m 3H<br>1.62–1.94 tt 2H<br>2.24–2.36 t 2H<br>2.31–2.56 q 2H<br>3.00–3.14 t 2H<br>3.07–3.22 t 2H<br>7.28 s 1H |
| 12 | pale yellow oil bpt = 150–153° C. @ 0.3 mmHg | 313 | 4.49 | 0.90 t 6H<br>1.40–2.00 m 6H<br>2.20–2.50 m 4H<br>3.00–3.20 m 4H<br>7.30 s 1H |
| 13 | yellow oil bpt = 120–124° C. @ 0.02 mmHg | 312 | 4.41 | 0.88–1.00 t 6H<br>1.08–1.95 m 8H<br>2.27–2.45 m 4H<br>3.03–3.20 m 4H<br>7.25 s 1H |
| 14 | yellow oil bpt = 126–129° C. @ 0.02 mm Hg | 313 | 4.44 | 0.80–1.07 m 9H<br>1.38–1.97 m 7H<br>2.21–2.54 m 4H<br>2.99–3.31 q 4H<br>7.31 s 1H |
| 15 | yellow oil | 308 | 4.21 | 0.74–1.08 t 9H<br>1.34–1.99 m 7H<br>2.42–2.61 m 4H<br>2.88–3.29 m 4H<br>7.30 s 1H |
| 16 | yellow oil | 316 | 4.16 | 0.71–0.99 t 3H<br>1.31–2.08 m 4H<br>2.33–2.61 t 2H<br>2.91–3.27 m 4H<br>6.96 s 1H<br>7.37 s 5H |
| 17 | yellow oil bpt = 155–157° C. @ 0.1 mm Hg | 317.8 | 4.44 | 0.79–1.17 t 3H<br>1.15 s 6H<br>1.45–1.92 m 4H<br>2.14 s 2H<br>2.26 s 2H<br>2.19–2.47 t 2H<br>3.01–3.30 t 4H |
| 18 | yellow oil bpt = 137–139° C. @ 0.2 mmHg | 319 | 4.49 | 0.95 d 6H<br>1.00 s 6H<br>1.40–2.00 m 5H<br>2.00–2.5 m 6H<br>3.1–3.3 m 4H |
| 19 | yellow solid mpt = 113° C. | 302 | 4.22 | 1.04 s 6H<br>1.74–2.09 m 2H<br>2.36 s 2H<br>2.74–2.60 m 4H<br>3.70–3.91 t 2H<br>7.67–8.02 m 4H |
| 20 | pale yellow mpt = 112–114° C. | 300 | 4.44 | 1.00 s 6H<br>1.65–2.01 m 2H<br>2.27–2.58 m 6H<br>3.53–3.71 t 2H<br>3.80 s 3H<br>6.96–7.33 m 4H |
| 21 | yellow waxy solid | 303 | 4.31 | 1.00 s 6H<br>1.64–2.04 m 2H<br>2.27 s 2H<br>2.41 s 2H<br>3.48–3.78 m 2H<br>3.87 s 3H<br>6.80–7.72 q 4H |
| 22 | yellow solid | 301.8 | 4.21 | 0.80–1.06 m 3H<br>0.99 s 6H<br>1.06–2.08 m 8H<br>2.27 s 2H<br>2.43 s 2H<br>2.58–2.76 t 2H<br>3.56–3.77 t 2H<br>7.19–7.59 q 4H |

EXAMPLE 38

1-[1-(3-methylbutyl)-1,4,5,6-tetrahydro-3-pyridyl]pentan-2,5-dione (38)

1-[1-(3-methylbutyl)-1,4,5,6-tetrahydro-3-pyridyl]pentan-2,5-dione can be prepared from 1-(3-pyridyl)pentan-2,5-dione [obtained by the method of Steller and Bchreckenburg *Chem. Ber.*, 1078, 2453 (1974)] according to the procedure of Example 14 parts (a) and (b).

EXAMPLE 39

Sunscreen compositions were prepared using the components shown in table 2.

| Part | Material | % w/w |
|---|---|---|
| A | Water | 69.5 |
| B | Polypropylene glycol Meristyl Ether | 20.0 |
|   | Glyceryl Stearate | 5.0 |
|   | Oleth 10 surfactant | 5.0 |
|   | Effective component | 0.5 |
| C | BHT antioxidant<br>Sodium thiosulphate | 0.02/0.2 |

Separate emulsion formulations were prepared using a mixture of parts A and B for each of compounds No. 3, 5, 13 and 18 as the effective component and the pH was adjusted to 7 by dropwise addition of 1M NaOH.

Further compositions were prepared using a mixture of part A, B and C for each of compounds 3, 5, 13 and 18 as the effective component.

We claim:

1. A compound of formula I

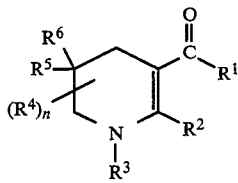

wherein:
$R^1$ is selected from the group consisting of $C_1$ to $C_{18}$ alkyl; $C_1$ to $C_9$ alkyl substituted with a substituent selected from the group consisting of hydroxy, amino, $C_1$ to $C_9$ alkoxy, $C_2$ to $C_9$ alkenyloxy, $C_1$ to $C_9$ alkanoyl, ($C_1$ to $C_9$ alkoxy) carbonyl, carbamoyl, ($C_1$ to $C_6$ alkyl)carbamoyl and phenyl; $C_2$ to $C_{18}$ alkenyl; $C_2$ to $C_9$ alkenyl substituted with a substituent selected from the group consisting of hydroxy, amino, $C_1$ to $C_9$ alkoxy, $C_2$ to $C_9$ alkenyloxy, $C_1$ to $C_9$ alkanoyl, carbamoyl, ($C_1$ to $C_6$ alkyl)carbamoyl, and phenyl; $C_2$ to $C_{18}$ alkynyl; phenyl; benzyl; the groups phenyl and benzyl substituted on the benzene ring with a substituent selected from the group of $C_1$ to $C_{12}$ alkyl, $C_1$ to $C_{12}$ alkoxy, $C_2$–$C_9$ alkylene, $C_2$ to $C_{12}$ alkenyloxy, $C_1$ to $C_{12}$ alkylamino N,N-di($C_1$ to $C_6$ alkyl)amino, ($C_1$ to $C_{12}$ alkoxy)carbonyl and $C_1$ to $C_{12}$ alkanoyl; $C_5$ to $C_7$ cycloalkyl; $C_5$ to $C_7$ cycloalkenyl; the groups substituted $C_5$ to $C_7$ cycloalkyl and substituted $C_5$ to $C_7$ cycloalkenyl wherein the substituent is selected from the group consisting of hydroxy, amino, $C_1$ to $C_9$ alkyl, $C_1$ to $C_9$ alkoxy, and $C_1$ to $C_9$ alkenyloxy;

$R^3$ is selected from the group consisting of $C_2$ to $C_{18}$ alkyl; $C_1$ to $C_9$ alkyl substituted with a substituent selected from the group consisting of hydroxy, amino, $C_1$ to $C_9$ alkoxy, $C_2$ to $C_9$ alkenyloxy, $C_1$ to $C_9$ alkanoyl, ($C_1$ to $C_9$ alkoxy)carbonyl, carbamoyl, ($C_1$ to $C_6$ alkyl)carbamoyl and phenyl; $C_2$ to $C_{18}$ alkenyl; $C_2$ to $C_9$ alkenyl substituted with a substituent selected from the group consisting of hydroxy, amino, $C_1$ to $C_9$ alkoxy, $C_2$ to $C_9$ alkenyloxy, $C_1$ to $C_9$ alkanoyl, ($C_1$ to $C_9$ alkoxy)carbonyl, carbamoyl, ($C_1$ to $C_9$ alkyl) carbamoyl and phenyl; $C_2$ to $C_{18}$ alkynyl; phenyl; benzyl; benzoyl; the groups phenyl, benzyl and benzoyl optionally substituted on the benzene ring with a substituent selected from the group consisting of hydroxy, amino, $C_1$ to $C_{12}$ alkyl, $C_2$ to $C_{12}$ alkenyl, $C_1$ to $C_{12}$ alkoxy, $C_2$ to $C_{12}$ alkenyloxy, $C_1$ to $C_{12}$ alkylamino, N,N-di($C_1$ to $C_6$ alkyl)amino, ($C_1$ to $C_{12}$ alkoxy)carbonyl, and $C_1$ to $C_{12}$ alkanoyl; $C_5$ to $C_7$ cycloalkyl; $C_5$ to $C_7$ cycloalkenyl; the groups substituted $C_5$ to $C_7$ cycloalkyl and substituted $C_5$ to $C_7$ cycloalkenyl wherein the substituent is selected from the group consisting of hydroxy, amino, $C_1$ to $C_9$ alkyl, $C_1$ to $C_9$ alkoxy, and $C_1$ to $C_9$ alkenyloxy; $C_1$ to $C_{18}$ alkanoyl; $C_2$ to $C_9$ alkanoyl substituted with a substituent selected from the group consisting of hydroxy, amino, $C_1$ to $C_9$ alkoxy, $C_2$ to $C_9$ alkenyloxy, $C_1$ to $C_9$ alkanoyl, carbamoyl, $C_1$ to $C_6$ alkyl)carbamoyl, ($C_1$ to $C_9$ alkoxy)carbonyl and phenyl; and the group —OROR$^9$ wherein R which may be the same or different are bivalent hydrocarbon radicals of 2 to 6 carbon atoms and $R^9$ is a hydrocarbon radical selected from $C_1$ to $C_6$ alkyl, $C_2$ to $C_6$ alkenyl phenyl, benzyl, ($C_1$ to $C_6$ alkyl) phenyl and ($C_1$ to $C_6$ alkyl)-benzyl;

$R^2$ is selected from the group consisting of hydrogen, $C_1$ to $C_6$ alkyl, $C_1$ to $C_6$ alkoxy;

$R^4$ is selected from the group consisting of $C_1$ to $C_6$ alkyl and $C_1$ to $C_6$ alkoxy;

n is an integer selected from 0 to 4 inclusive;

$R^5$ and $R^6$ which may be the same or different are selected from hydrogen, $C_1$ to $C_6$ alkyl, $C_1$ to $C_6$ alkoxy, $C_1$ to $C_{10}$ alkanoyl, $C_1$ to $C_{10}$ alkanoyl substituted by carboxyl or ($C_1$ to $C_6$ alkoxy) carbonyl;

with the proviso that when $R^1$ is methyl then $R^3$ is not selected from the group of hydroxyethyl, methoxymethyl and benzyl and when $R^1$ is phenol, $R^3$ is not acetyl or alkyl substituted with phenyl.

2. A compound according to claim 1 wherein: $R^1$ is selected from $C_1$ to $C_{18}$ alkyl; $C_1$ to $C_9$ alkyl substituted with a substituent selected from the group consisting of hydroxy, amino, $C_1$ to $C_9$ alkoxy, $C_1$ to $C_9$ alkanoyl and ($C_1$ to $C_9$ alkoxy)carbonyl; $C_1$ to $C_{18}$ alkenyl; cyclohexyl; phenyl; benzyl; the groups phenyl and benzyl said groups being substituted in the benzene ring with a substituent selected from the group of $C_1$, to $C_9$ alkyl, $C_2$ to $C_9$ alkenyl, $C_1$ to $C_9$ alkoxy, $C_1$ to $C_9$ alkanoyl and ($C_1$ to $C_9$ alkoxy) carbonyl;

$R^3$ is selected from $C_2$ to $C_{18}$ alkyl; $C_1$ to $C_9$ alkyl substituted with a substituent selected from the group consisting of hydroxy, amino, $C_1$ to $C_9$ alkoxy and $C_1$ to $C_9$ alkanoyl; $C_2$ to $C_{18}$ alkenyl; cyclohexyl; phenyl; benzyl; benzoyl; the groups phenyl, benzyl and benzoyl said groups being substituted on the benzene ring with a substituent selected from the group of $C_1$ to $C_9$ alkyl, $C_2$ to $C_9$ alkenyl, $C_1$ to $C_9$ alkoxy, $C_1$ to $C_9$ alkanoyl and ($C_1$ to $C_9$ alkoxy)carbonyl; $C_3$ to $C_{18}$ alkanoyl; and $C_2$ to $C_9$ alkanoyl substituted with phenyl;

$R^2$ is hydrogen or $C_1$ or $C_6$ alkyl;

$R^4$ is $C_1$ to $C_6$ alkyl;

n is from 0 to 4;

$R^5$ and $R^6$ are independently selected from hydrogen; $C_1$ to $C_6$ alkyl; the substituted alkanoyl group of formula III

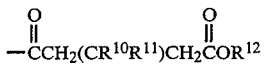

wherein $R^{10}$, $R^{11}$ and $R^{12}$ are independently selected from $C_1$ to $C_4$ alkyl and hydrogen.

3. A compound according to claim 2 wherein:
$R^1$ is selected from the group consisting of $C_1$ to $C_{18}$ alkyl; $C_1$ to $C_6$ alkyl substituted with a substituent selected from $C_1$ to $C_6$ alkanoyl and ($C_1$ to $C_6$ alkoxy) carboxyl; $C_1$ to $C_{18}$ alkenyl; phenyl, and benzyl;
$R^2$ is hydrogen or $C_1$ to $C_4$ alkyl;
$R^3$ is selected from the group consisting of $C_2$ to $C_{18}$ alkyl; $C_1$ to $C_9$ alkyl substituted with a substituent selected from the group consisting of hydroxy and $C_1$ to $C_9$ alkoxy; $C_1$ to $C_{18}$ alkenyl; benzoyl; benzyl; benzoyl substituted with a substituent selected from $C_1$ to $C_6$ alkyl and $C_1$ to $C_6$ alkoxy; and $C_3$ to $C_9$ alkanoyl; $R^4$ is $C_1$ to $C_4$ alkyl; and n is an integer from 0 to 3;
$R^5$ and $R^6$ are selected from the group consisting of: (i) $R^5$ and $R^6$ are independently selected from hydrogen and $C_1$ to $C_4$ alkyl and (ii) one of $R^5$ and $R^6$ is hydrogen and the other is a group of formula III

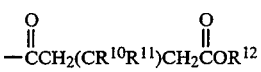

wherein $R^{10}$, $R^{11}$ and $R^{12}$ are independently selected from the group consisting of hydrogen and $C_1$ to $C_4$ alkyl.

4. A compound according to claim 3 wherein:
$R^1$ is $C_1$ to $C_9$ alkyl;
$R^2$ is selected from hydrogen and $C_1$ to $C_4$ alkyl;
$R^3$ is selected from $C_2$ to $C_9$ alkyl; $C_2$ to $C_9$ alkenyl; $C_1$ to $C_9$ alkyl substituted with a substituent selected from hydroxy, phenyl and $C_1$ to $C_6$ alkoxy; benzoyl; benzoyl substituted with a substituent selected from the group consisting of $C_1$ to $C_6$ alkyl and $C_1$ to $C_6$ alkoxy; and $C_3$ to $C_9$ alkanoyl;
$R^4$ is $C_1$ to $C_4$ alkyl;
n is from 0 to 3;
$R^5$ and $R^6$ are consisting of
(i) $R^5$ and $R^6$ are independently selected from hydrogen and $C_1$ to $C_4$ alkyl; and
(ii) one of $R^5$ and $R^6$ is hydrogen and the other is a group of formula III

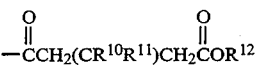

wherein $R^{10}$ and $R^{11}$ are methyl and $R^{12}$ is hydrogen or $C_1$ to $C_6$ alkyl and wherein when one of $R^5$ and $R^6$ is not hydrogen or $C_1$ to $C_4$ alkyl, then n is zero.

5. A compound according to claim 3 wherein:
$R^1$ is $C_1$ to $C_9$ alkyl;
$R^2$ is hydrogen;
$R^3$ is selected from the group consisting of $C_1$ to $C_9$ alkyl; 2-phenylethyl and cyclohexyl;
$R^4$ is methyl
n is chosen from 0 to 3;
$R^5$ and $R^6$ are selected from the group consisting of (i) $R^5$ and $R^6$ are independently selected from hydrogen and methyl; and (ii) one of $R^5$ and $R^6$ is hydrogen and the other is a group of formula III

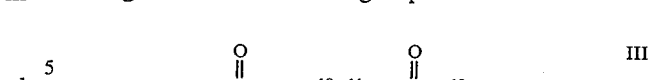

wherein $R^{10}$ and $R^{11}$ are methyl and $R^{12}$ is ethyl; and wherein when at least one of $R^5$ and $R^6$ is not hydrogen or methyl, then n is zero.

6. A compound of formula

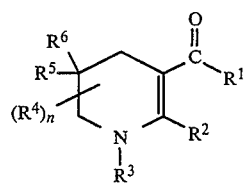

where $R^5$ and $R^6$ are independently selected from the group consisting of hydrogen, $C_1$ to $C_6$ alkyl and $C_1$ to $C_6$ alkoxy and $R^1$, $R^2$, $R^3$, $R^4$ and n are as defined according to claim 1.

7. A compound according to claim 6 wherein $R^5$ and $R^6$ are independently selected from hydrogen and $C_1$ to $C_6$ alkyl.

8. A compound according to claim 7 wherein $R^5$ and $R^8$ are hydrogen.

9. A compound according to claim 3 wherein:
$R^1$ is $C_1$ to $C_{18}$ alkyl;
$R^2$ is hydrogen;
$R^3$ is selected from the group consisting of $C_2$ to $C_{18}$ alkyl and $C_2$ to $C_{18}$ alkenyl;
n is O;
$R^5$ and $R^6$ are hydrogen.

10. A compound according to claim 6 wherein:
$R^1$ is selected from the group consisting of methyl, ethyl, propyl, 3-methylbutyl;
$R^2$ is hydrogen;
$R^3$ is selected from the group consisting of propyl, 1-methylethyl, butyl, 3-methylbutyl, 2-ethylhexyl, and 3-methyl-2-butenyl;
n is 0; and
$R^5$ and $R^6$ are hydrogen.

11. A compound selected from the group consisting of
methyl 1-(3-methylbutyl)-1,4,5,6-tetrahydro-3-pyridyl ketone;
methyl 1-(3-methyl-2-butenyl)-1,4,5-6-tetrahydro-3-pyridyl ketone;
ethyl 1-butyl-1,4,5,6-tetrahydro-3-pyridyl ketone;
ethyl 1-(3-methylbutyl)-1,4,5,6-tetrahydro-3-pyridyl ketone;
propyl 1-propyl-1,4,5,6-tetrahydro-3-pyridyl ketone;
propyl 1-butyl-1,4,5,6-tetrahydro-3-pyridyl ketone;
propyl-1-(3-methylbutyl)-1,4,5,6-tetrahydro-3-pyridyl ketone;
4-methylpentyl 1-propyl-1,4,5,6-tetrahydro-3-pyridyl ketone;
phenyl 1-propyl-1,4,5,6-tetrahydro-3-pyridyl ketone; and
methyl 1-butyl-4,4,6 trimethyl-1,4,5,6-tetrahydro-3-pyridyl ketone.

* * * * *